US012672799B2

(12) United States Patent
Harshman et al.

(10) Patent No.: US 12,672,799 B2
(45) Date of Patent: **\*Jul. 7, 2026**

(54) IDENTIFICATION, QUANTITATION AND ANALYSIS OF UNIQUE BIOMARKERS IN SWEAT

(71) Applicant: Government of the United States, as represented by the Secretary of the Air Force, Wright-Patterson AFB, OH (US)

(72) Inventors: Sean W. Harshman, Fairborn, OH (US); Anthony V. Qualley, Washington Township, OH (US); Nicole M. Schaeublin, Beavercreek, OH (US); Jennifer A. Martin, Beavercreek, OH (US); Claude C. Grigsby, Xenia, OH (US); Rhonda L. Pitsch, Springfield, OH (US)

(73) Assignee: United States of America as represented by the Secretary of the Air Force, Wright-Patterson AFB, OH (US)

( \* ) Notice: Subject to any disclaimer, the term of this patent is extended or adjusted under 35 U.S.C. 154(b) by 383 days.

This patent is subject to a terminal disclaimer.

(21) Appl. No.: 18/151,978

(22) Filed: Jan. 9, 2023

(65) Prior Publication Data

US 2023/0165488 A1 Jun. 1, 2023

Related U.S. Application Data

(63) Continuation of application No. 16/431,326, filed on Jun. 4, 2019, now Pat. No. 11,547,326.

(Continued)

(51) Int. Cl.
*A61B 5/1455* (2006.01)
*A61B 5/00* (2006.01)
(Continued)

(52) U.S. Cl.
CPC ........ *A61B 5/14517* (2013.01); *A61B 5/4866* (2013.01); *A61B 5/4875* (2013.01);
(Continued)

(58) Field of Classification Search
CPC . A61B 5/14517; A61B 5/4866; A61B 5/4875; A61B 5/6802; A61B 5/7275;
(Continued)

(56) References Cited

U.S. PATENT DOCUMENTS

2018/0020966 A1 1/2018 Begtrup et al.
2018/0249919 A1 9/2018 Pont et al.
(Continued)

OTHER PUBLICATIONS

D. L. Lee et al., "Global untargeted metabolic profiling of human sweat from exercising men and woman," J. Int'l Soc. Sports Nutrition, vol. 8 (2011) 9-10.
(Continued)

*Primary Examiner* — Marjan Fardanesh
(74) *Attorney, Agent, or Firm* — AFMCLO/JAZ; Eugene P. Sunday

(57) ABSTRACT

A biomarker diagnostic system includes a sensor to collect a sweat sample from a biological subject; a processor operatively connected to the sensor, wherein the processor is configured to perform metabolic and proteomic profiling of biomarkers in the sweat sample. The metabolic and proteomic profile is compared to a predetermined profile of the biomarkers and to determine a physiological status of the biomarkers. The system further includes a feedback unit operatively coupled to the sensor and the processor and configured to output physiological performance data based on the physiological status.

13 Claims, 10 Drawing Sheets

Related U.S. Application Data

(60) Provisional application No. 62/680,228, filed on Jun. 4, 2018.

(51) Int. Cl.
| | |
|---|---|
| *A61B 5/145* | (2006.01) |
| *G01N 33/68* | (2006.01) |
| *G16B 40/00* | (2019.01) |

(52) U.S. Cl.
CPC .......... *A61B 5/6802* (2013.01); *A61B 5/7275* (2013.01); *G01N 33/6848* (2013.01); *G16B 40/00* (2019.02); *G01N 2560/00* (2013.01)

(58) Field of Classification Search
CPC ............ A61B 5/14507; A61B 10/0064; G16B 40/00; G01N 33/6848; G01N 2560/00
See application file for complete search history.

(56) References Cited

U.S. PATENT DOCUMENTS

| | | |
|---|---|---|
| 2019/0110722 A1 | 4/2019 | Ionescu et al. |
| 2019/0290248 A1 | 9/2019 | Katchman et al. |
| 2020/0049654 A1 | 2/2020 | Kajisa et al. |
| 2020/0077936 A1 | 3/2020 | Cunningham et al. |

OTHER PUBLICATIONS

M. M. Raiszadeh et al., "Proteomic analysis of eccrine sweat: implications for the discovery of schizophrenia biomarker proteins," J Proteome Res., vol. 11 (2012) 2127-2139.

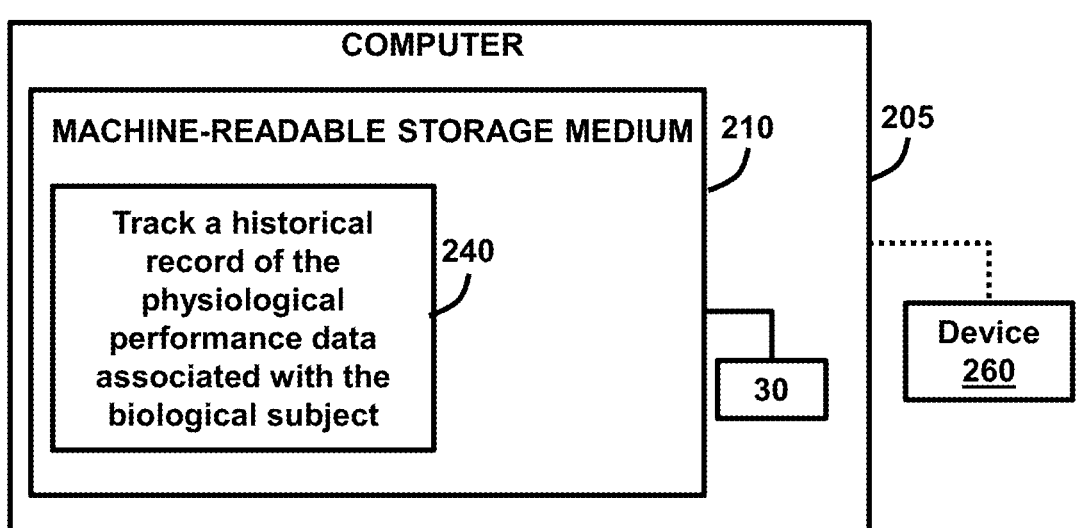

200

COMPUTER

MACHINE-READABLE STORAGE MEDIUM | 210

205

Track a historical record of the physiological performance data associated with the biological subject | 240

30

Device
260

FIG. 9B

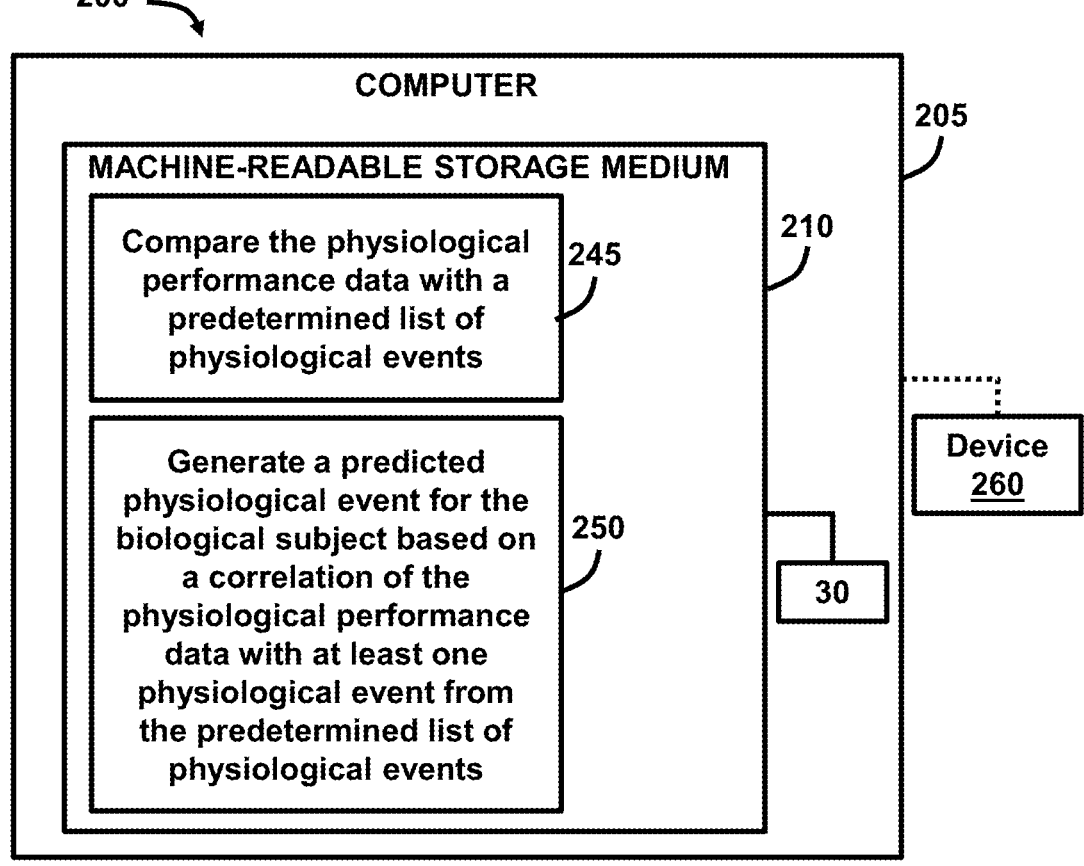

200

COMPUTER

205

MACHINE-READABLE STORAGE MEDIUM

Compare the physiological performance data with a predetermined list of physiological events | 245

210

Generate a predicted physiological event for the biological subject based on a correlation of the physiological performance data with at least one physiological event from the predetermined list of physiological events | 250

30

Device
260

IDENTIFICATION, QUANTITATION AND ANALYSIS OF UNIQUE BIOMARKERS IN SWEAT

This application is a continuation of U.S. application Ser. No. 16/431,326 filed Jun. 4, 2019 and issued as U.S. Pat. No. 11,547,326 on Jan. 10, 2023, which claimed the benefit of and priority to prior filed U.S. Provisional Application No. 62/680,228, filed on Jun. 4, 2018. The specifications of these applications are incorporated herein by reference in its entirety, each in its entirety.

RIGHTS OF THE GOVERNMENT

The invention described herein may be manufactured and used by or for the Government of the United States for all government purposes without the payment of any royalty.

FIELD OF THE INVENTION

The present invention relates generally to bioinformatics and, more particularly, to diagnostic techniques based on biomarkers.

BACKGROUND OF THE INVENTION

Non-invasive and accurate access of biomarkers remains a "Holy Grail" of the biomedical community. Human eccrine sweat is a surprisingly biomarker-rich fluid, which is gaining increasing attention, especially in applications of continuous bio-monitoring where access to other biofluids prove more challenging, if not impossible. Sweat is a biofluid that may be passively and non-invasively collected with potential links to important physiological states that are known to impact human physical and cognitive performance. Although human sweat has been studied for several decades, excreted sweat remains an often-overlooked media source for biomarker discovery due to the relatively low abundance of analytes. Sweat has been shown to be composed of low quantities of electrolytes, small molecules, proteins, and lipids. The majority of sweat research has revolved around pH, chloride ions, sodium ions, potassium ions, ammonia, urea, and lactate. However, recent biomarker discovery approaches, such as mass spectrometry and NMR spectroscopy, have been applied to expand the understanding of this media.

Beyond the mechanics of gathering sweat for analysis, as described in U.S. Patent Application Publication No. 2015/0057515, the complete disclosure of which, in its entirety, is herein incorporated by reference, the accurate identification, collection, and quantitation of appropriate biomarkers in sweat remains a challenge. Biomarkers include chemicals carried in bodily fluids that may provide significant information to enable diagnosis of ailments, health status, toxins, performance, and other physiological attributes even in advance of any physical sign, symptom, or presentation.

Sweat, as a biofluid, has several attractive attributes. However, investigation into sweat for biomarker discovery applications is still in its infancy. Studies on the proteomic and metabolomic content of sweat suggest analytes are both in low abundance and dominated, primarily, by defense related proteins and amino acids. Although relatively few proteins in sweat have been identified (as compared to other media sources, such as blood or tissue lysates), there is a potential for sweat to hold proteins for biomarker discovery. Some research demonstrates evidence for a differential abundance of sweat proteins between control and schizophrenia patients. Other research demonstrates that active tuberculosis has a more diverse sweat proteome than control and healthy controls. Similarly, sweat metabolomics has provided evidence for lung cancer diagnostics. Additionally, the same group showed differences in metabolomic abundances between active (exercise) and passive (stimulated) sweat.

Accordingly, sweat has recently gained popularity as a potential tool for diagnostics and biomarker monitoring because its collection is non-invasive and its composition may depend on one or more health related conditions, such as those identified above. However, analyzing sweat for biomarkers presents several questions, including methods of collection, methods of analysis, and how does the information on biomarkers obtainable from sweat relate to biomarkers in blood serum.

Some conventional methods for collecting and analyzing biomarkers in sweat are known, such as described those described in U.S. Application Publication Nos. 2016/0262667, 2016/0374598, and 2015/0057515, the disclosures of which are incorporated herein by reference, each in its entirety. Yet, these solutions are directed primarily at electrolyte monitoring to detect hydration and fatigue states. Other solutions are directed at identifying circulating biomarkers, typically from a bodily fluid, that may be used in profiling of physiological states or determining phenotypes, such as those described in U.S. Patent Application Publication Nos. 2003/0015208 and 2006/0172429 as well as WO Publication No. 2012174282, the disclosures of which are incorporated herein by reference, each in its entirety. Such circulating biomarkers include nucleic acids, proteins, and circulating structures such as vesicles, and nucleic acid-protein complexes. However, these solutions do not provide for the ability to predict, diagnose, or evaluate events, disease, or heath or through sweat detection.

As such, there remains a need for methods of collection and analyzing biomarkers in sweat that may have diagnostic value or indicative of health.

SUMMARY OF THE INVENTION

The present invention overcomes the foregoing problems and other shortcomings, drawbacks, and challenges of conventional methods of collecting and analyzing biomarkers in sweat. While the invention will be described in connection with certain embodiments, it will be understood that the invention is not limited to these embodiments. To the contrary, this invention includes all alternatives, modifications, and equivalents as may be included within the spirit and scope of the present invention.

In view of the foregoing, and in accordance with embodiments of the present invention, a biomarker diagnostic system includes a sensor to collect a sweat sample from a biological subject, a processor operatively connected to the sensor, and a feedback unit operatively connected to the sensor and the processor. The processor is configured to perform metabolic and proteomic profiling of biomarkers in the sweat sample by comparing the metabolic and proteomic profiling with a predetermined profile of the biomarkers and determining a physiological status of the biomarkers based on the comparison. The feedback unit is to output physiological performance data based on the physiological status.

The sensor may comprise a wearable exercise-tracking device attached to the biological subject. The physiological performance data may comprise any of hydration data, nutrition data, physical exertion status data, and recovery data for the biological subject. The feedback unit may be configured to output the physiological performance data, in real-time, as the biological subject is undergoing physical activity during which the sweat sample is collected, based on a real-time determination of the physiological status of the biomarkers by the processor. The sensor may be configured to continuously collect sweat samples from the biological subject. The processor may be configured to continuously perform metabolic and proteomic profiling of biomarkers in the sweat sample, compare the metabolic and proteomic profiling with the predetermined profile of the biomarkers, and determine the physiological status of the biomarkers based on a continuous collection of the sweat samples by the sensor. The feedback unit may be configured to continuously output the physiological performance data based on the continuous collection of the sweat samples by the sensor. The processor may be configured to perform a data analytics assessment based on the physiological status to determine a physiological event prediction of the biological subject. The feedback unit may be configured to output a signal based on the physiological event prediction determined by the processor.

According to other embodiments of the present invention, a diagnostic method includes non-invasively collecting a sweat sample from a biological subject undergoing physical activity and performing metabolic and proteomic profiling of biomarkers in the collected sweat sample. The metabolic and proteomic profile is compared with a predetermined profile of the biomarkers such that a physiological status of the biomarkers may be determined.

The method may include freezing the sweat sample after collection. The physiological status may comprise an identification of the biomarkers. The physiological status may comprise an identification of diseases associated with the biomarkers. The physiological status may comprise an identification of a health status of the biological subject based on a metabolomic profile of the biomarkers in the collected sweat sample. The physiological status may comprise an identification of a health status of the biological subject based on a proteomic profile of the biomarkers in the collected sweat sample. The method may comprise correlating the physiological status with predetermined activity performance metrics associated with the biological subject.

Yet other embodiments of the present invention are directed to a machine-readable storage medium comprising computer-executable instructions that, when executed, cause a processor of an electronic device to perform metabolic and proteomic profiling of biomarkers in sweat samples of a biological subject that is undergoing a fluctuation in physical activity over a predetermined period of time. The metabolic and proteomic profiles are compared with a predetermined profile of the biomarkers to determine whether there is a correlation between the biomarkers in the sweat samples and the predetermined profile of the biomarkers and a physiological status of the biomarkers is determined. Physiological performance data based on the physiological status is generated and a signal output the physiological performance data to alert the biological subject.

The instructions, when executed, may be configured to cause the processor to track a historical record of the physiological performance data associated with the biological subject. The instructions, when executed, further cause the processor to compare the physiological performance data with a predetermined list of physiological events. A predicted physiological event for the biological subject based on a correlation of the physiological performance data with at least one physiological event from the predetermined list of physiological events may be generated. The instructions, when executed, further cause the processor to generate different signals to output based on different predicted physiological events.

Additional objects, advantages, and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIG. 9B is a block diagram illustrating a system to track records used with the processing of biomarkers associated with sweat samples, according to an embodiment of the present invention.

FIG. 9C is a block diagram illustrating a system to generate predicted physiological events used with the processing of biomarkers associated with sweat samples, according to an embodiment of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 1:
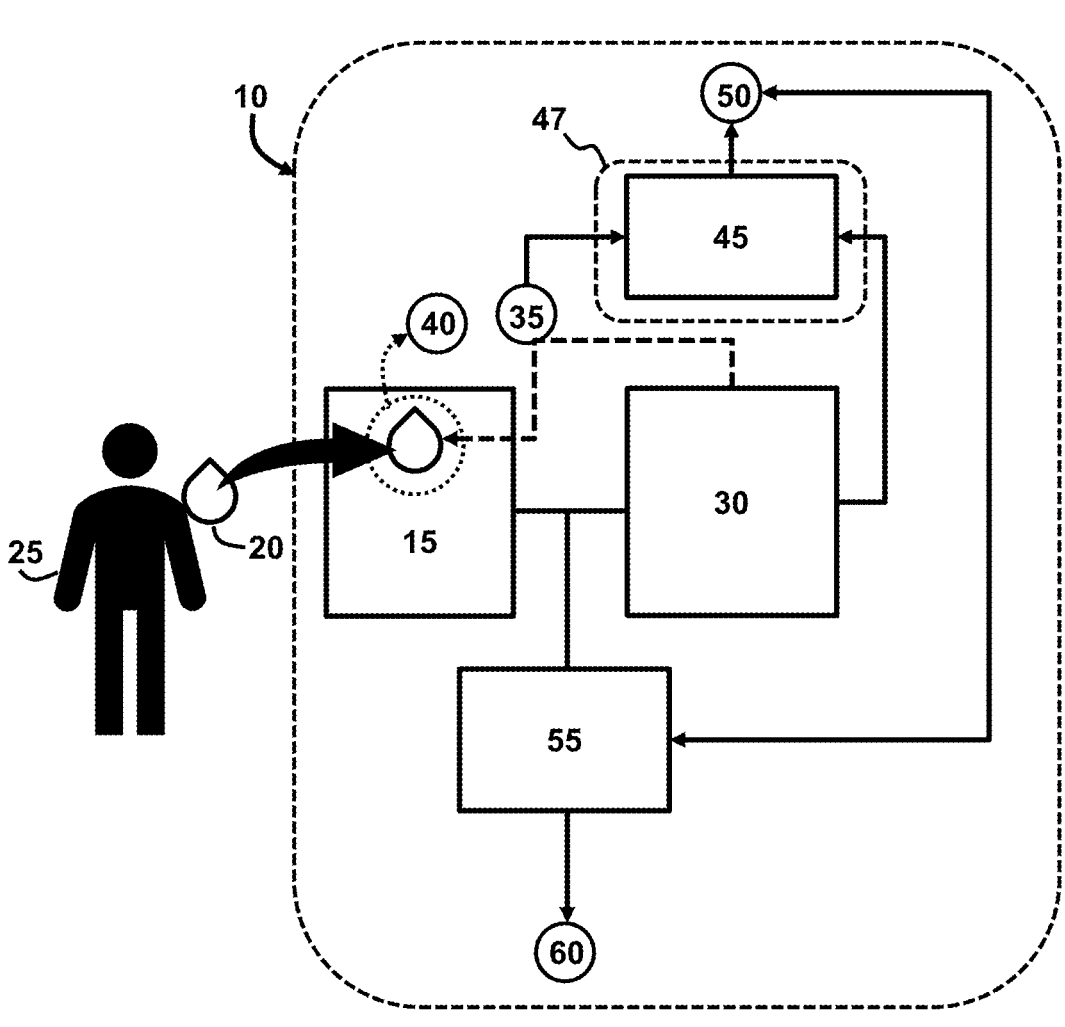
FIG. 1 is a schematic block diagram illustrating a biomarker diagnostic system, according to an embodiment of the present invention.

Referring now to the drawings, and more particularly to FIG. 1, where similar reference characters denote corresponding features consistently throughout, there are shown exemplary embodiments (although the size and relative sizes of components, layers, and regions, etc. may be exaggerated for clarity), a biomarker diagnostic system 10 according to an embodiment of the present invention is described. The biomarker diagnostic system 10 includes a sensor 15 to collect a sweat sample 20 from a biological subject 25. In some examples, the sensor 15 may comprise any of an electrical sensor, a chemical sensor, a mechanical sensor, or a combination thereof used to collect the sweat sample 20 from the biological subject 25. The sensor 15 may be directly attached to the biological subject 25 or may be operatively connected to the biological subject 25 with an intervening component (not shown), which may be used to assist with the collection of the sweat sample 20.

According to various embodiments, the biological subject 25 may be a human or may be any other biological subject capable of producing and excreting sweat. The amount/ volume of the sweat sample 20 that is collected may be any suitable minimal amount/volume necessary to conduct diagnostic bio/chemical testing thereupon.

The sensor 15 may collect the sweat sample 20 itself or may initiate or include another mechanism (such as the intervening component) to conduct the collection of the sweat sample 20 upon the sensor 15 detecting the presence of the sweat sample 20 excreting from the biological subject 25.

Figure 2:
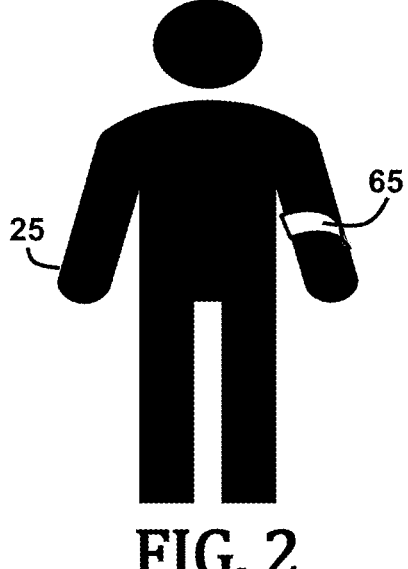
FIG. 2 is a schematic block diagram illustrating an aspect of a sensor in the biomarker diagnostic system of FIG. 1 and in accordance with an embodiment of the present invention.

For instance, in the embodiment illustrated in FIG. 2, the sensor 15 may comprise a wearable exercise tracking device 65 that may be removably attached to an arm 66 of the biological subject 25; however, the wearable exercise tracking device 65 may be configured to be attached to any part of the biological subject that is capable of detecting the presence of the sweat sample 20 excreted by the biological subject 25. Collection of the sweat sample 20 an include a suitable collection mechanism, as described above, that may be part of the sensor 15 or part of another device or mechanism that may be operatively coupled to the sensor 15.

The biomarker diagnostic system 10 further includes a processor 30 operatively coupled to the sensor 15. In some embodiments, the processor 30 (and various other processing devices described herein and illustrated in the figures) may be embodied as hardware-enabled modules and may be configured as a plurality of overlapping or independent electronic circuits, devices, and discrete elements packaged onto a circuit board to provide data and signal processing functionality within a computer, an electronic device, or both. An example might be a comparator, inverter, or flip-flop, which could include a plurality of transistors and other supporting devices and circuit elements. The modules that are configured with electronic circuit process computer logic instructions capable of providing digital signals, analog signals, or both for performing various functions as described herein. The various functions may further be embodied and physically saved as any of data structures, data paths, data objects, data object models, object files, database components. For example, the data objects may be configured as a digital packet of structured data.

The data structures could be configured as any of an array, tuple, map, union, variant, set, graph, tree, node, and an object, which may be stored and retrieved by computer memory and may be managed by processors, compilers, and other computer hardware components. The data paths may be configured as part of a computer CPU that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), or complex operations (e.g., using single clock calculations, sequential calculations, iterative calculations, etc.).

The data objects may be configured as physical locations in computer memory and may be a variable, a data structure, or a function. In the embodiments configured as relational databases (e.g., such ORACLE relational databases), the data objects may be configured as a table or column. Other configurations include specialized objects, distributed objects, object-oriented programming objects, and semantic web objects, for example. The data object models may be configured as an application-programming interface for creating HyperText Markup Language (HTML) and Extensible Markup Language (XML) electronic documents. The models may be further configured as any of a tree, graph, container, list, map, queue, set, stack, or variations thereof. The data object files are created by compilers and assemblers and contained generated binary code and data for a source file. The database components can include any of tables, indexes, views, stored procedures, and triggers.

According to various embodiments, the processor 30 may be configured to determine a profile 35 that is a digital representation a metabolic profile, a proteomic profile, or both of the amino acids, proteins, and so forth (collectively, biomarkers 40) of the sweat sample 20. According to one particular embodiment, building the profile 35 may include retrieving data from a biological database, a biochemical database, or both to analyze the biomarkers 40 in the sweat sample 20. The processor 30 may further compare the profile 35 data output with a predetermined profile 45 of biomarkers, which may include presence or absence of certain biomarkers, concentrations of biomarkers, and correlations of the presence/absence, concentration, or both to a physiological status 50. In that regard, the processor 30 may compare the profile 35 specific to the particular biological subject 25 to the database, the predetermined profile 45, or both determine whether a match of stored biomarkers exist in the predetermined profile 45. In another embodiment, the predetermined profile 45 may be stored in memory 47 and retrieved by the processor 30 for analysis and comparison. In some embodiments, the memory 47 may be Random Access Memory (RAM), Read-Only Memory (ROM), a cache memory, hard drive storage, flash memory, or other type of storage mechanism. According to an embodiment, the predetermined profile 45 may be a stored list of data that allows the processor 30 to compare bio/chemical signatures associated with the biomarkers 40 from the sweat sample 20. In other embodiments, any of the processor 30 and memory 47 may be part of the sensor 15. In still other embodiments, the processor 30, the memory 47, or both may be part of another subsystem apart from the sensor 15, but which is communicatively or operatively linked to the sensor 15 through any of wired and wireless connections. Furthermore, any of the processor 30 and the memory 47 may be part of a server computer system or electronic device (not shown) that is remotely linked to the sensor 15 through any of wired and wireless communication.

The processor 30 is further configured to determine the physiological status 50 of the biological subject 25 based on the profile 35 and the comparison. According to one embodiment, the physiological status 50 may describe a biomarker profile of the amino-acid based biomarkers 40. In another embodiment, the physiological status 50 may comprise metadata of the bio/chemical signatures associated with the biomarkers 40. Still, in another embodiment, the physiological status 50 may comprise a computer-generated health assessment report identifying medical-related prognosis associated with the biological subject 25 based on an assessment of the combination of the biomarkers 40 present in the sweat sample 20. In one aspect of the embodiments herein, the processor 30 may perform data normalization processing of the data associated with the bio/chemical signatures of the biomarkers 40 using any suitable data normalization technique or algorithm.

The biomarker diagnostic system 10 may further include a feedback unit 55 operatively connected to the sensor 15 and the processor 30 and configured to output physiological performance data 60 based on the physiological status 50. The feedback unit 55 may be part of the sensor 15 or it may be a separate component. According to one embodiment, the feedback unit 55 may comprise any of a display screen, a speaker, and a motor to output the physiological performance data 60. In some embodiments, the physiological performance data 60 may be output as images, video, alphanumeric characters, and any other type of symbols that are displayed by the feedback unit 55. In other embodiments, the physiological performance data 60 may be output as an audio signal that may include any type of sound, ringtone, music, computer-generated words or any suitable audio format that is stored as an audio file in the memory 47, for example, and capable of being processed by the processor 30 for output by the feedback unit 55. In another embodiment, the physiological performance data 60 may be output as mechanical vibration caused by a motor (not shown) in the feedback unit 55 that may be offset and weighted causing a vibration upon rotation. In some embodiments, the processor 30 may determine the type of output of the physiological performance data 60 to be generated based on the physiological status 50 that is determined by the processor 30. Moreover, in some embodiments, a combination of different types of output (i.e., audio, video, and/or vibration) may be output as the physiological performance data 60. According to one embodiment, the physiological performance data 60 may comprise any type of biometric data associated with the biological subject 25 and which is capable of being determined using an analysis of the sweat sample 20 such as the heart rate, pulse, etc. among other types of biometric data.

According to the embodiments of the present invention, novel biomarkers 40 may be identified (which is distinct from standard laboratory analyses such as chloride, pH, and lactic acid), associated with the sweat sample 20 and exercise generating the sweat sample 20 to non-invasively monitor changes in the personal physiology of the biological subject 25. In one embodiment, the sweat sample 20 contains amino acids and electrolytes derived from plasma. There are numerous examples of biomarkers 40 and other small molecules that may be identified in the sweat sample 20 including proline, valine, threonine, leucine/isoleucine, glutamic acid, citrulline, urocanic acid, and nonanedioic acid. Other biomarkers 40 include any of α-amino-adipic acid, asparagine, aspartate, glutamic acid, glycine, histidine, hydroxylysine, isoleucine, leucine, lysine, ornithine, phenylalanine and serine, as well as α-amino-butyric acid, glutamine, cystine and proline or alanine, and threonine. A list of exemplary proteins that may be identified in the sweat sample 20 is provided in Table 1.

TABLE 1

List of proteins in sweat samples

| DESCRIPTION | Short Name | UNIPROT Accession No. |
|---|---|---|
| sp\|P12273\|PIP_HUMAN Prolactin-inducible protein OS = *Home sapiens* GN = PIP PE = 1 SV = 1 | Dermcidin | P81605 |
| sp\|P81605\|DCD_HUMAN Dermcidin OS = *Homo sapiens* GN = DCD PE = 1 SV = 2 | Cystatin-A | P01040 |
| sp\|P0CG48\|UBC_HUMAN Polyubiquitin-C OS = *Homo sapiens* GN = UBC PE = 1 SV = 3 | Ubiquitin-60S ribosomal protein L40 | P62987 |
| *cRAP*sp\|P00761\|TRYP_PIG Trypsin OS = *Sus scrofa* PE = 1 SV = 1 | Keratin, type II cytoskeletal 2 epidermal | P35908 |
| sp\|P02768\|ALBU_HUMAN Serum albumin OS = *Homo sapiens* GN = ALB PE = 1 SV = 2 | Suprabasin | Q6UWP8 |
| sp\|P25311\|ZA2G_HUMAN Zinc-alpha-2-glycoprotein OS = *Homo sapiens* GN = AZGP1 PE = 1 SV = 2 | Desmoglein-1 | Q02413 |
| sp\|P31944\|K1C10_HUMAN Capase-14 OS = *Homo sapiens* GN = CASP14 PE = 1 SV = 2 | Nucleobindin-1 | Q02818 |
| sp\|P31944\|K1C10_HUMAN Keratin; type I cytoskeletal 10 OS = *Homo sapiens* GN = KRT10 PE = 1 SV = 6 | Corneodesmosin | Q15517 |
| sp\|O95969\|SG1D2_HUMAN Secretoglobin family 1D member 2 OS = *Homo sapiens* GN = SCGB1D2 PE = 2 SV = 1 | Arginase-1 | P05089 |

TABLE 1-continued

List of proteins in sweat samples

| DESCRIPTION | Short Name | UNIPROT Accession No. |
|---|---|---|
| sp\|P16870\|CBPE_HUMAN Carboxypeptidase E OS = *Homo sapiens* GN = CPE PE = 1 SV = 1 | Glyceraldehyde-3-phosphate dehydrogenase | P04406 |
| sp\|P04264\|K2C1_HUMAN Keratin; type II cytoskeletal 1 OS = *Homo sapiens* GN = KRT1 PE = 1 SV = 6 | Proteasome subunit alpha type-7 | O14818 |
| *cRAP*sp\|P02769\|ALBU_BOVIN Serum albumin OS = *Bos Taurus* GN = ALB PE = 1 SV = 4 | Cystatin-M | Q15828 |
| sp\|Q02413\|DSG1_HUMAN Desmoglein-1 OS = *Homo sapiens* GN = DSG1 PE = 1 SV = 2 | Phosphatidylethanolamine-binding protein 1 | P30086 |
| sp\|P01040\|CYTA_HUMAN Cystatin-A OS = *Homo sapiens* GN = CSTA PE = 1 SV = 1 | Glutaredoxin-1 | P35754 |
| sp\|P29508\|SPB3_HUMAN Serpin B3 OS = *Homo sapiens* GN = SERPINB3 PE = 1 SV = 2 | Prolactin-inducible protein | P12273 |
| sp\|P02787\|TRFE_HUMAN Serotransferrin OS = *Homo sapiens* GN = TF PE = 1 SV = 3 | Protein S100-A7 | P31151 |
| sp\|O75223\|GGCT_HUMAN Gamma-glutamylcyclotransferase OS = *Homo sapiens* GN = GGCT PE = 1 SV = 1 | Beta-2-microglobulin | P61769 |
| sp\|Q06828\|FMOD_HUMAN Fibromodulin OS = *Homo sapiens* GN = FMOD PE = 1 SV = 2 | Proteasome subunit alpha type-1 | P25786 |
| sp\|P35908\|K22E_HUMAN Keratin; type II cytoskeletal 2 epidermal OS = *Homo sapiens* GN = KRT2 PE = 1 SV = 2 | Annexin A2 | P07355 |
| sp\|Q08188\|TGM3_HUMAN Protein-glutamine gamma-glutamyltransferase E OS = *Homo sapiens* GN = TGM3 PE = 1 SV = 4 | Desmocollin-1 | Q08554 |
| sp\|P10599\|THIO_HUMAN Thioredoxin OS = *Homo sapiens* GN = TXN PE = 1 SV = 3 | Serpin B3 | P29508 |
| sp\|P09668\|CATH_HUMAN Pro-cathepsin H OS = *Homo sapiens* GN = CTSH PE = 1 SV = 4 | Filaggrin | P20930 |
| sp\|P01834\|IGKC_HUMAN Ig kappa chain C region OS = *Homo sapiens* GN = IGKC PE = 1 SV = 1 | Polyubiquitin-B | P0CG47 |
| sp\|P35527\|K1C9_HUMAN Keratin; type I cytoskeletal 9 OS = *Homo sapiens* GN = KRT9 PE = 1 SV = 3 | Protein-glutamine gamma-glutamyltransferase E | Q08188 |
| sp\|P10909\|CLUS_HUMAN Clusterin OS = *Homo sapiens* GN = CLU PE = 1 SV = 1 | Clusterin | P10909 |
| sp\|P48594\|SPB4_HUMAN Serpin B4 OS = *Homo sapiens* GN = SERPINB4 PE = 1 SV = 2 | Proteasome subunit alpha type-3 | P25788 |
| sp\|P01857\|IGHG1_HUMAN Ig gamma-1 chain C region OS = *Homo sapiens* GN = IGHG1 PE = 1 SV = 1 | Beta-1,3-N-acetylglucosaminyltransferase lunatic | Q8NES3 |
| sp\|P61769\|B2MG_HUMAN Beta-2-microglobulin OS = *Homo sapiens* GN = B2M PE = 1 SV = 1 | Proteasome subunit beta type-5 | P28074 |
| sp\|Q7Z794\|K2C1B_HUMAN Keratin; type II cytoskeletal 1b OS = *Homo sapiens* GN = KRT77 PE = 2 SV = 3 | Peroxiredoxin-2 | P32119 |
| sp\|Q96DR8\|MUCL1_HUMAN Mucin-like protein 1 OS = *Homo sapiens* GN = MUCL1 PE = 1 SV = 1 | Bleomycin hydrolase | Q13687 |
| sp\|O60911\|CATL2_HUMAN Cathepsin L2 OS = *Homo sapiens* GN = CTSV PE = 1 SV = 2 | Catalase | P04040 |
| sp\|Q8NBJ4\|GOLM1_HUMAN Golgi membrane protein 1 OS = *Homo sapiens* GN = GOLM1 PE = 1 SV = 1 | Caspase-14 | P31944 |
| sp\|P04259\|K2C6B_HUMAN Keratin; type II cytoskeletal 6B OS = *Homo sapiens* GN = KRT6B PE = 1 SV = 5 | Thioredoxin | P10599 |
| sp\|P31151\|S10A7_HUMAN Protein S100-A7 OS = *Homo sapiens* GN = S100A7 PE = 1 SV = 4 | Histidine--tRNA ligase, cytoplasmic | P12081 |
| sp\|P55000\|SLUR1_HUMAN Secreted Ly-6/uPAR-related protein 1 OS = *Homo sapiens* GN = SLURP1 PE = 1 SV = 2 | Glutathione synthetase | P48637 |
| sp\|P0CG09\|LAC3_HUMAN Ig lambda-3 chain C regions OS = *Homo sapiens* GN = IGLC3 PE = 1 SV = 1 | | |
| sp\|P00441\|SODC_HUMAN Superoxide dismutase [Cu—Zn] OS = *Homo sapiens* GN = SOD1 PE = 1 SV = 2 | | |
| sp\|P04040\|CATA_HUMAN Catalase OS = *Homo sapiens* GN = CAT PE = 1 SV = 3 | | |
| sp\|P01009\|A1AT_HUMAN Alpha-1-antitrypsin OS = *Homo sapiens* GN = SERPINA1 PE = 1 SV = 3 | | |
| sp\|Q96P63\|SPB12_HUMAN Serpin B12 OS = *Homo sapiens* GN = SERPINB12 PE = 1 SV = 1 | | |
| sp\|O75882\|ATRN_HUMAN Attractin OS = *Homo sapiens* GN = ATRN PE = 1 SV = 2 | | |
| sp\|P68871\|HBB_HUMAN Hemoglobin subunit beta OS = *Homo sapiens* GN = HBB PE = 1 SV = 2 | | |
| sp\|P07339\|CATD_HUMAN Cathepsin D OS = *Homo sapiens* GN = CTSD PE = 1 SV = 1 | | |
| sp\|P61626\|LYSC_HUMAN Lysozyme C OS = *Homo sapiens* GN = LYZ PE = 1 SV = 1 | | |
| sp\|P01861\|IGHG4_HUMAN Ig gamma-4 chain C region OS = *Homo sapiens* GN = IGHG4 PE = 1 SV = 1 | | |
| sp\|P02533\|K1C14_HUMAN Keratin; type I cytoskeletal 14 OS = *Homo sapiens* GN = KRT14 PE = 1 SV = 4 | | |
| sp\|Q8IW75\|SPA12_HUMAN Serpin A12 OS = *Homo sapiens* GN = SERPINA12 PE = 1 SV = 1 | | |

TABLE 1-continued

List of proteins in sweat samples

| DESCRIPTION | Short Name | UNIPROT Accession No. |
|---|---|---|
| sp|O75635|SPB7_HUMAN Serpin B7 OS = *Homo sapiens* GN = SERPINB7 PE = 1 SV = 1 | | |
| sp|P01023|A2MG_HUMAN Alpha-2-macroglobulin OS = *Homo sapiens* GN = A2M PE = 1 SV = 3 | | |
| sp|Q15828|CYTM_HUMAN Cystatin-M OS = *Homo sapiens* GN = CST6 PE = 1 SV = 1 | | |
| sp|P48668|K2C6C_HUMAN Keratin; type II cytoskeletal 6C OS = *Homo sapiens* GN = KRT6C PE = 1 SV = 3 | | |
| sp|P20933|ASPG_HUMAN N(4)-(beta-N-acetylglucosaminyl)-L-asparaginase OS = *Homo sapiens* GN = AGA PE = 1 SV = 2 | | |
| sp|P01859|IGHG2_HUMAN Ig gamma-2 chain C region OS = *Homo sapiens* GN = IGHG2 PE = 1 SV = 2 | | |
| sp|P60174|TPIS_HUMAN Triosephosphate isomerase OS = *Homo sapiens* GN = TPI1 PE = 1 SV = 3 | | |
| sp|O95274|LYPD3_HUMAN Ly6/PLAUR domain-containing protein 3 OS = *Homo sapiens* GN = LYPD3 PE = 1 SV = 2 | | |
| sp|Q99497|PARK7_HUMAN Protein deglycase DJ-1 OS = *Homo sapiens* GN = PARK7 PE = 1 SV = 2 | | |
| sp|P13647|K2C5_HUMAN Keratin; type II cytoskeletal 5 OS = *Homo sapiens* GN = KRT5 PE = 1 SV = 3 | | |
| *cRAP*sp|O77727|K1C15_SHEEP Keratin; type I cytoskeletal 15 OS = *Ovis aries* GN = KRT15 PE = 2 SV = 1 | | |
| sp|P30086|PEBP1_HUMAN Phosphatidylethanolamine-binding protein 1 OS = *Homo sapiens* GN = PEBP1 PE = 1 SV = 3 | | |
| sp|Q99574|NEUS_HUMAN Neuroserpin OS = *Homo sapiens* GN = SERPINI1 PE = 1 SV = 1 | | |
| sp|P50452|SPB8_HUMAN Serpin B8 OS = *Homo sapiens* GN = SERPINB8 PE = 1 SV = 2 | | |
| sp|P60709|ACTB_HUMAN Actin; cytoplasmic 1 OS = *Homo sapiens* GN = ACTB PE = 1 SV = 1 | | |
| sp|P07858|CATB_HUMAN Cathepsin B OS = *Homo sapiens* GN = CTSB PE = 1 SV = 3 | | |
| sp|Q7Z3Y7|K1C28_HUMAN Keratin; type I cytoskeletal 28 OS = *Homo sapiens* GN = KRT28 PE = 1 SV = 2 | | |
| sp|P07686|HEXB_HUMAN Beta-hexosaminidase subunit beta OS = *Homo sapiens* GN = HEXB PE = 1 SV = 3 | | |
| sp|Q04695|K1C17_HUMAN Keratin; type I cytoskeletal 17 OS = *Homo sapiens* GN = KRT17 PE = 1 SV = 2 | | |
| sp|Q08554|DSC1_HUMAN Desmocollin-1 OS = *Homo sapiens* GN = DSC1 PE = 1 SV = 2 | | |
| sp|P49862|KLK7_HUMAN Kallikrein-7 OS = *Homo sapiens* GN = KLK7 PE = 1 SV = 1 | | |
| sp|P02774|VTDB_HUMAN Vitamin D-binding protein OS = *Homo sapiens* GN = GC PE = 1 SV = 1 | | |
| sp|Q9NZH8|IL36G_HUMAN Interleukin-36 gamma OS = *Homo sapiens* GN = IL36G PE = 1 SV = 1 | | |
| sp|P05109|S10A8_HUMAN Protein S100-A8 OS = *Homo sapiens* GN = S100A8 PE = 1 SV = 1 | | |
| sp|P56537|IF6_HUMAN Eukaryotic translation initiation factor 6 OS = *Homo sapiens* GN = EIF6 PE = 1 SV = 1 | | |
| sp|Q08380|LG3BP_HUMAN Galectin-3-binding protein OS = *Homo sapiens* GN = LGALS3BP PE = 1 SV = 1 | | |
| sp|P52758|UK114_HUMAN Ribonuclease UK114 OS = *Homo sapiens* GN = HRSP12 PE = 1 SV = 1 | | |
| sp|P35754|GLRX1_HUMAN Glutaredoxin-1 OS = *Homo sapiens* GN = GLRX PE = 1 SV = 2 | | |
| sp|P02647|APOA1_HUMAN Apolipoprotein A-I OS = *Homo sapiens* GN = APOA1 PE = 1 SV = 1 | | |
| sp|P06731|CEAM5_HUMAN Carcinoembryonic antigen-related cell adhesion molecule 5 OS = *Homo sapiens* GN = CEACAM5 PE = 1 SV = 3 | | |
| sp|P12821|ACE_HUMAN Angiotensin-converting enzyme OS = *Homo sapiens* GN = ACE PE = 1 SV = 1 | | |
| sp|Q86SG5|S1A7A_HUMAN Protein S100-A7A OS = *Homo sapiens* GN = S100A7A PE = 1 SV = 3 | | |
| sp|P54652|HSP72_HUMAN Heat shock-related 70 kDa protein 2 OS = *Homo sapiens* GN = HSPA2 PE = 1 SV = 1 | | |
| sp|Q92820|GGH_HUMAN Gamma-glutamyl hydrolase OS = *Homo sapiens* GN = GGH PE = 1 SV = 2 | | |
| sp|P16083|NQO2_HUMAN Ribosyldihydronicotinamide dehydrogenase OS = *Homo sapiens* GN = NQO2 PE = 1 SV = 5 | | |
| sp|Q9HB40|RISC_HUMAN Retinoid-inducible serine carboxypeptidase OS = *Homo sapiens* GN = SCPEP1 PE = 1 SV = 1 | | |
| sp|Q01469|FABP5_HUMAN Fatty acid-binding protein; epidermal OS = *Homo sapiens* GN = FABP5 PE = 1 SV = 3 | | |

TABLE 1-continued

List of proteins in sweat samples

| DESCRIPTION | Short Name | UNIPROT Accession No. |
|---|---|---|
| sp\|Q6P4A8\|PLBL1__HUMAN Phospholipase B-like OS = *Homo sapiens* GN = PLBD1 PE = 1 SV = 2 | | |
| sp\|P43251\|BTD__HUMAN Biotinidase OS = *Homo sapiens* GN = BTD PE = 1 SV = 2 | | |
| sp\|P11279\|LAMP1__HUMAN Lysosome-associated membrane glycoprotein 1 OS = *Homo sapiens* GN = LAMP1 PE = 1 SV = 3 | | |
| sp\|P61916\|NPC2__HUMAN Epididymal secretory protein E1 OS = *Homo sapiens* GN = NPC2 PE = 1 SV = 1 | | |
| sp\|P01037\|CYTN__HUMAN Cystatin-SN OS = *Homo sapiens* GN = CST1 PE = 1 SV = 3 | | |
| *cRAP*sp\|P04745\|AMY1__HUMAN Alpha-amylase 1 OS = *Homo sapiens* GN = AMY1A PE = 1 SV = 2 | | |

Intentionally left blank

The use of biomarkers 40 may comprise the system 10 as well as subsystems and modules that include analytical processes as well as communication protocols to compute and deliver the physiological performance data 60 through the feedback unit 55 using one of a number of transmission techniques, such as wired or wireless communications, which can provide for event prediction of the biological subject 25 and possible intervention.

Figure 3:
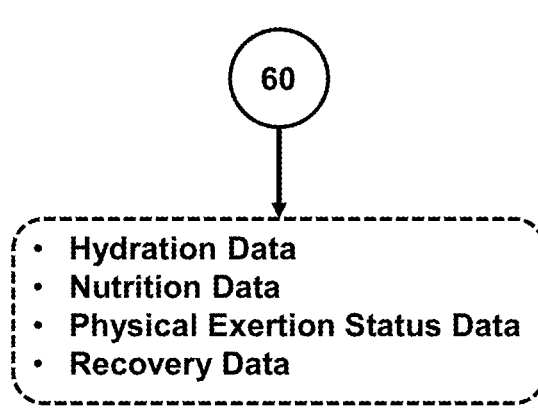
FIG. 3 is a schematic block diagram illustrating some aspects of the physiological performance data of the biomarker diagnostic system of FIG. 1 and in accordance with an embodiment of the present invention.

Referring now to FIG. 3, with continued reference to FIGS. 1 and 2, composition of the physiological performance data 60 is shown and may comprise one or more of hydration data, nutrition data, physical exertion status data, and recovery data for the biological subject 25. Furthermore, as described above, the physiological performance data 60 may comprise any suitable biometric data associated with the biological subject 25, and which may be capable of being assessed based on the analysis of the sweat sample 20. In some examples, the physiological performance data 60 may be output by the feedback unit 55 to provide an alert to the biological subject 25. For example, if the hydration data indicates that the biological subject 25 is becoming (or is) dehydrated, then the alert output by the feedback unit 55 may include the display of an image, video, or both of a cup of water by the feedback unit 55. Additionally or alternatively, the feedback unit 55 may provide an audio signal, which may be preprogrammed by the biological subject 25, associating a particular sound with a hydration reminder for the biological subject 25. Additionally or alternatively, a vibrational signal by the sensor 15, the feedback unit 55, the wearable exercise-tracking device 65, or a combination thereof may indicate that the biological subject 25 should review the physiological performance data 60.

According to still other embodiments, nutritional data of the physiological performance data 60 may indicate that the biological subject 25 has a low blood sugar level. An alert output by the feedback unit 55 to signal the low blood sugar may be the display of an image, or video, or both of food, with or without an audio and/or vibrational signal, by the feedback unit 55 may be provided. Nutritional information need not be limited to low blood sugar, but may include, for example, malnourishment. Such signals may prompt the biological subject 25 to monitor or review the physiological performance data 60.

According to still other embodiments, a physical exertion status data of the physiological performance data 60 may indicate that the biological subject 25 is over-exerting himself/herself and may faint, become exhausted, other. An alert output by the feedback unit 55 to signal the physical exertion may be the display of an image, or video, or both of a chair or bed, with or without audio and/or vibrational signal, by the feedback unit 55 may be provided. Such signals may prompt the biological subject 25 to monitor or review the physiological performance data 60.

According to still other embodiments, recovery data of the physiological performance data 60 may indicate that the biological subject 25 should rest. An alert output by the feedback unit 55 to signal the physical exertion may be the display of an image, or video, or both associated with physical recovery, with or without audio and/or vibrational signal, by the feedback unit 55 may be provided. Such signals may prompt the biological subject 25 to monitor or review the physiological performance data 60 and to take precautionary measures to ensure physical recovery is practiced.

Figure 4:
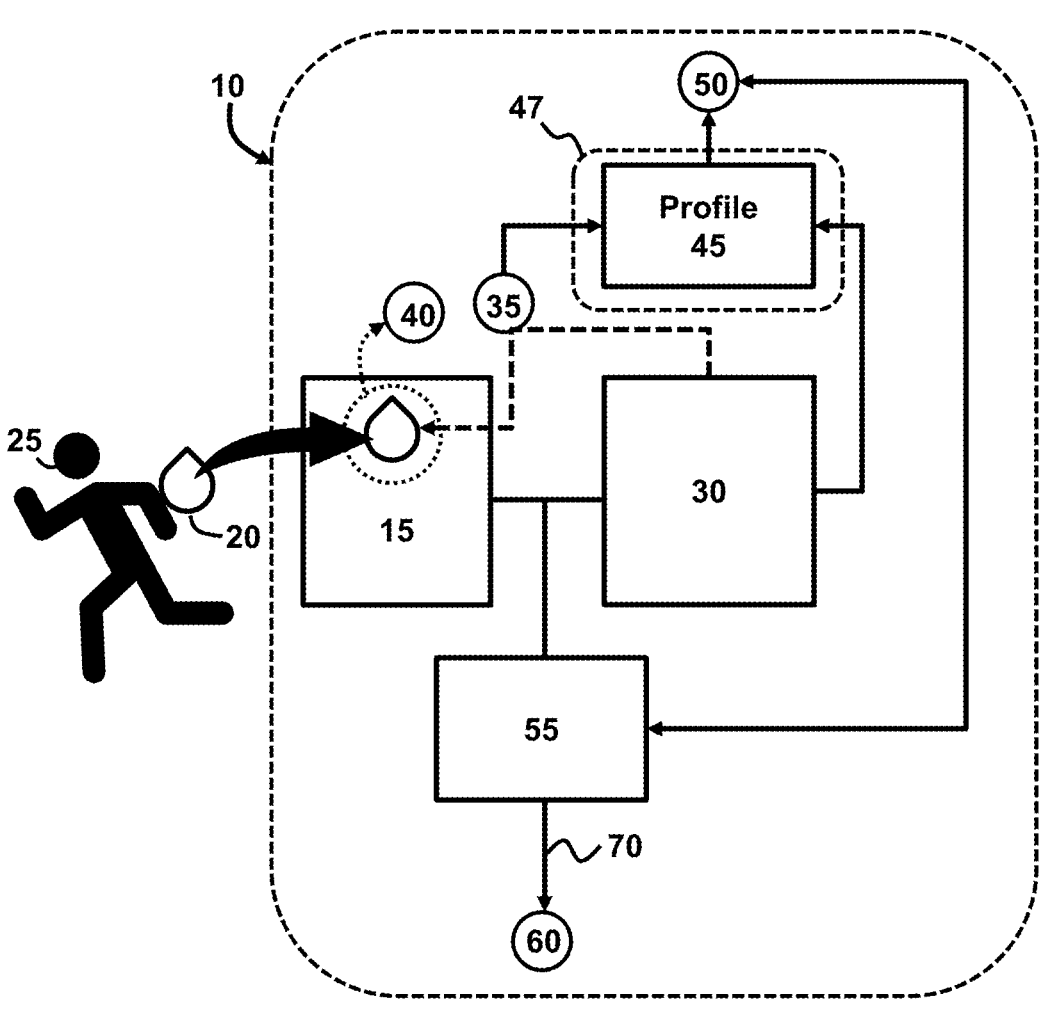
FIG. 4 is a schematic block diagram illustrating real-time processing by the biomarker diagnostic system of FIG. 1, according to an embodiment of the present invention.

Turning now to FIG. 4, with continued reference to FIGS. 1 and 2, the biomarker diagnostic system 10 is illustrated to further include an embodiment in which an output 70 by the feedback unit 55 of the physiological performance data 60 is provided in real-time. As such, monitoring may occur as the biological subject 25 is undergoing physical activity, during which the sweat sample 20 is continuously, periodically, or otherwise intermittently collected. The physiological status 50 of the biomarkers 40 by the processor 30 may also be determined continuously, periodically, or otherwise intermittently to provide real-time data. Metabolic and proteomic discovery efforts tend to rely on pilocarpine stimulated sweat from resting individuals; however these techniques may not be directly comparable to those subjects exercising; i.e., undergoing physical activity. As a result, embodiments described herein include collection of the sweat sample 20 from the biological subject 25 undergoing physical activity, i.e., exercising or otherwise enduring an aerobic activity.

In some embodiments, real-time determination of the physiological status 50 of the biomarkers 40 enable the output 70 to provide alerts, feedback, or both to the biological subject 25 during an exercise routine. As such, the biological subject 25 may monitor himself/herself (or otherwise be monitored) to reduce a likelihood of physical exhaustion or other type of health episode (i.e., heart attack, etc.). According to some embodiments, the feedback unit 55 may be communicatively linked to an emergency response system (not shown) such that the output 70 is automatically transmitted to the emergency response system. In this way, a medical responder, such as a paramedic, may be alerted of the health episode. Accordingly, the output 70 may further include geolocation data for enabling the emergency response system to identify a location of the feedback unit 55 transmitting the health emergency episode. Hence, the biological subject 25 may be located and the emergency responder may administer first aid or other care.

Figure 5:
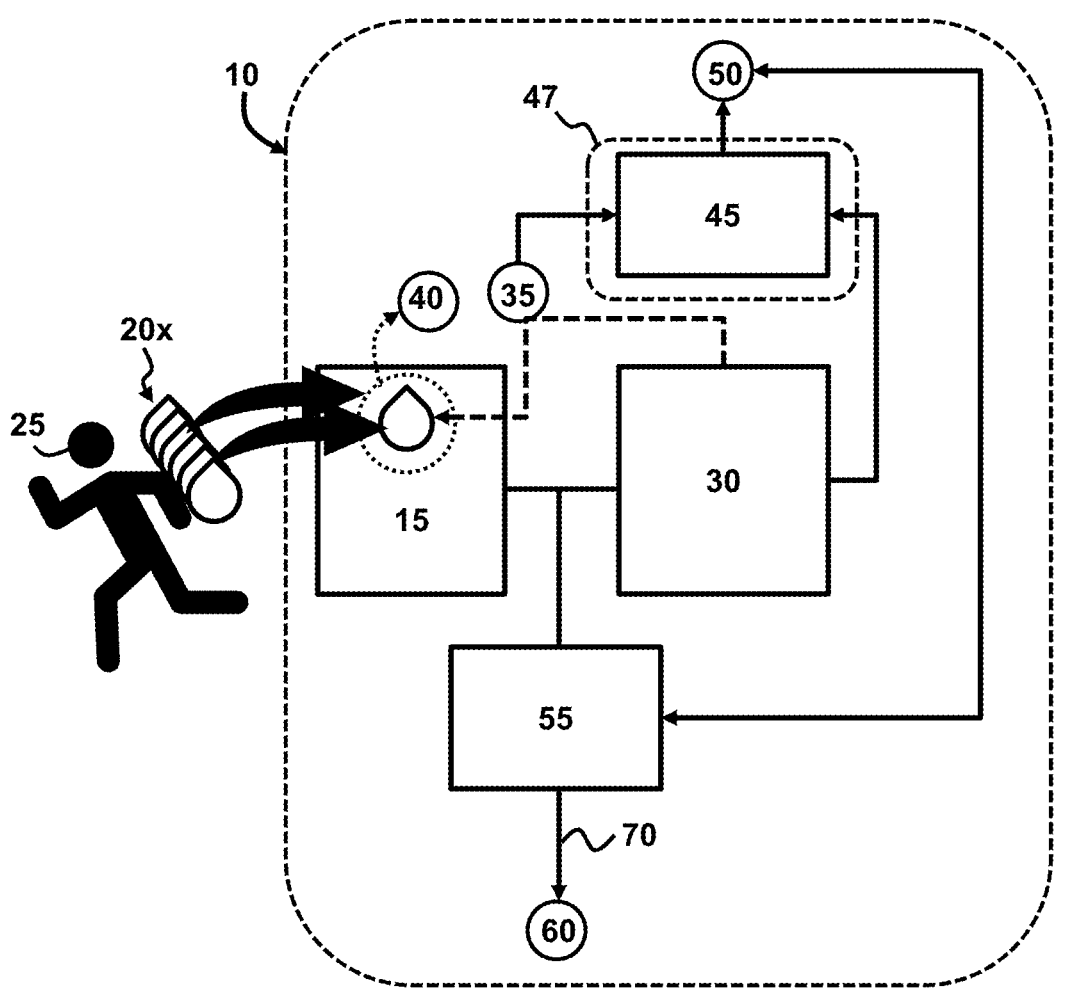
FIG. 5 is a schematic block diagram illustrating continuous processing of the biomarker diagnostic system of FIG. 1, according to an embodiment of the present invention.

Turning now to FIG. 5, with continued reference to FIGS. 1 and 2, the biomarker diagnostic system 10 is illustrated to continuously collect sweat samples (illustrated as 20x) from the biological subject 25. The sweat samples 20x may be collected over a predetermined period of time, which may be determined based on the physical activity of the biological subject 25. For example, the sensor 15 may continuously collect the sweat samples 20x so long as sweat is being excreted by the biological subject 25, a temperature of the biological subject 25 is elevated, a heart rate of the biological subject 25 is elevated, or a combination thereof. The sensor 15 and any associated collection mechanisms may be appropriately sized to ensure the complete collection of the sweat samples 20x from the biological subject 25 to permit a more accurate profile 35.

The processor 30 may be configured to continuously determine the profile 35 of the biomarkers 40 in the sweat samples 20x, compare the profile 35 with the predetermined profile 45 of the biomarkers 40, determine the physiological status 50 of the biomarkers 40 based on a continuous collection of the sweat samples 20x by the sensor 15, or a combination thereof. Moreover, the feedback unit 55 is configured to provide the continuously output 70 the physiological performance data 60 based on the continuous collection of the sweat samples 20x by the sensor 15. An ability to collect and monitor unique and appropriate sweat biomarkers, continuously and in real-time, enables the biological subject 25 to make informed decisions regarding hydration, nutrition, level of exertional, and recovery, which are all variables that moderate the physical performance data 60. Such ability provides great utility to the biological subject 25 under physical stress, particularly biological subjects 25 in the process of performing physical activity or exercise.

Additional utility of the embodiments herein is provided by the attribute that biomarkers 40 found in the sweat sample 20 may be exploited for the establishment of a unique biomarker-based profile configured to identify the unique biological subject 25. Due to the presence of a broad set of different, low molecular weight organic molecules and compounds, the sweat sample 20 may be a good candidate for the successfully diagnosing some pathologies.

Figure 6:
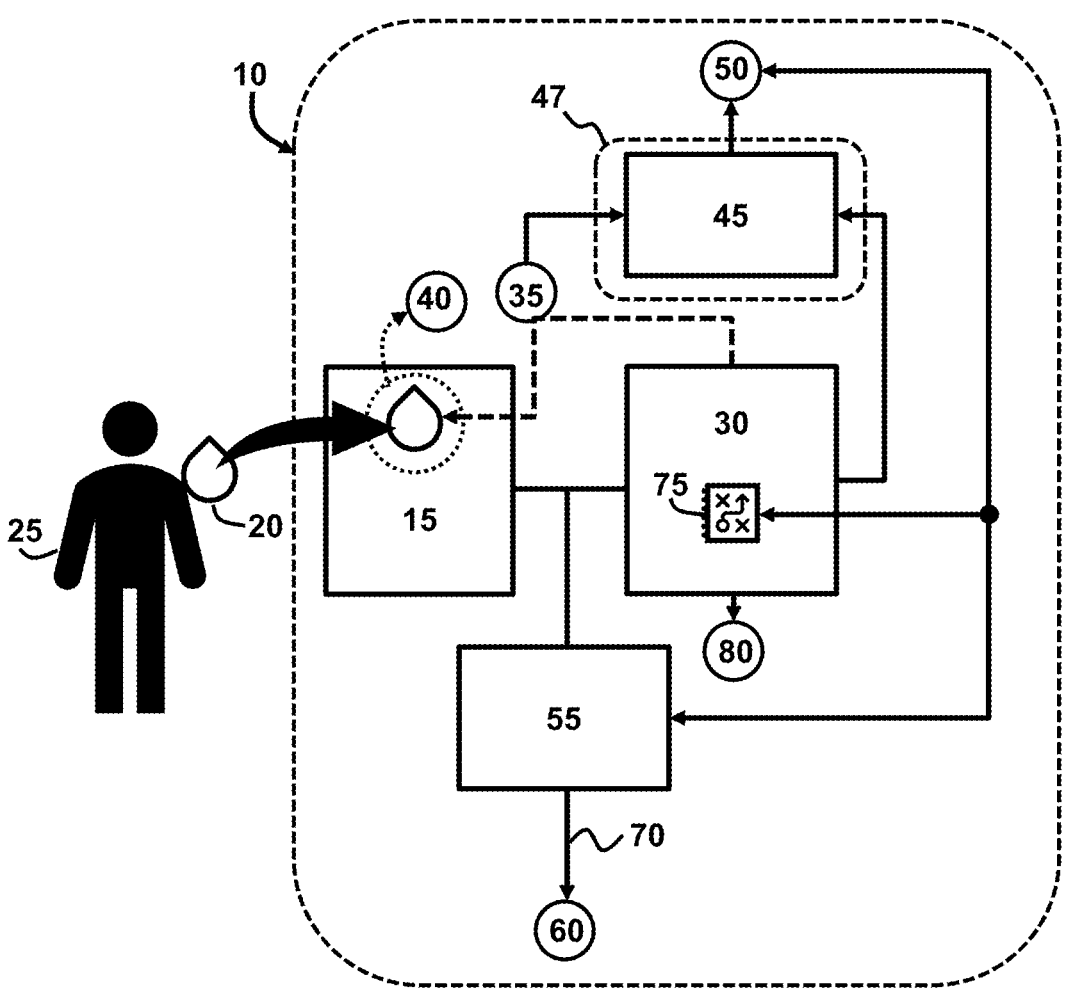
FIG. 6 is schematic block diagram illustrating a processor of the biomarker diagnostic system of FIG. 1 performing a data analytic process according to an embodiment of the present invention.

Referring now to FIG. 6, with continued reference to FIGS. 1 and 2, the biomarker diagnostic system 10 is illustrated to further include an embodiment in which the processor 30 is configured to perform a data analytics assessment 75 based on the physiological status 50 and determine a physiological event prediction 80 of the biological subject 25. The data analytics assessment 75 may provide a health/medical assessment of the biological subject 25 based on predetermined health profiles and risk factors associated with a similar physiological status 50 that are preprogrammed and processed by the processor 30. For example, the data analytics assessment 75 may determine whether the biological subject 25 is at risk of experiencing a particular physiological event (such as a heart attack, fainting, etc.) based on the physiological status 50. The data analytics assessment 75 may be based on real-time analysis of the sweat sample 20 (such as illustrated in FIG. 4), a continuous collection of sweat samples 20x (such as illustrated in FIG. 5), or both.

Figure 7:
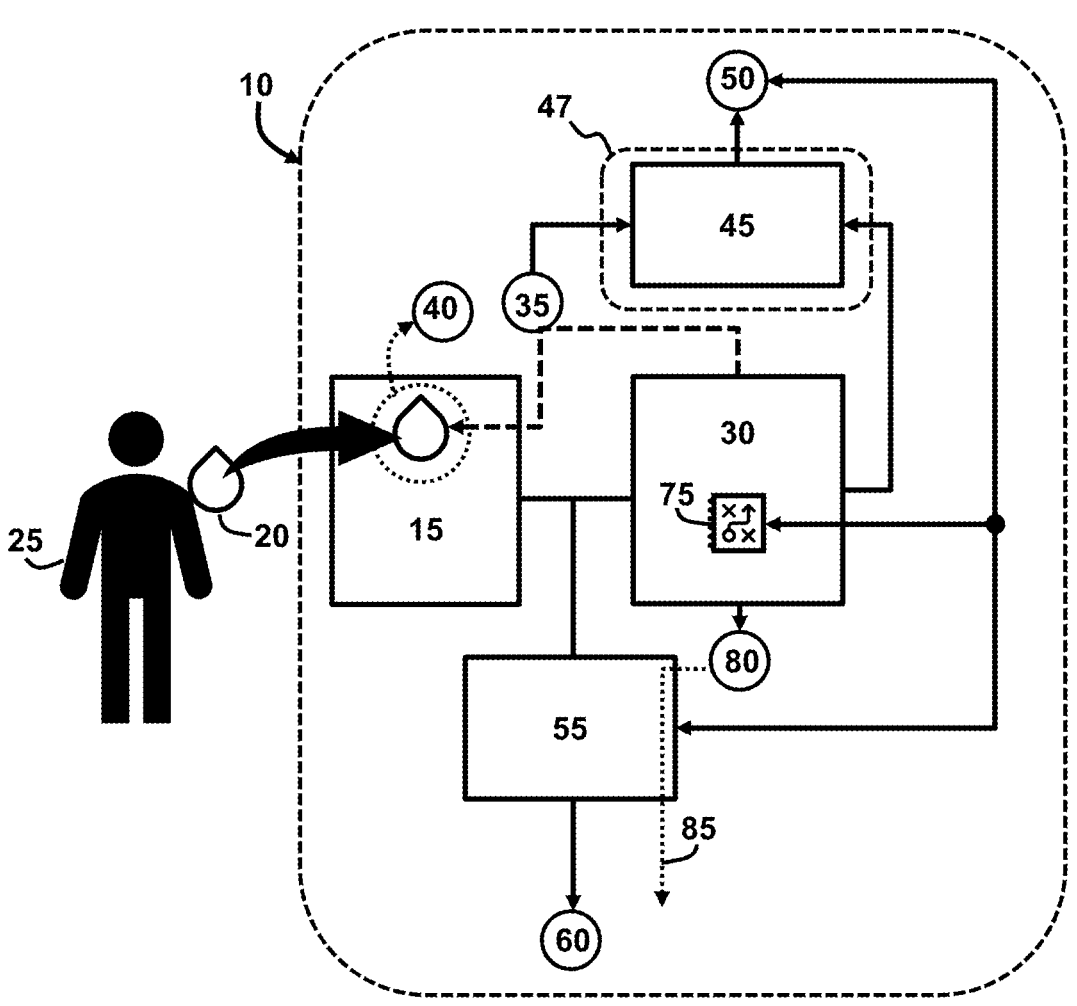
FIG. 7 is schematic block diagram illustrating an aspect of a feedback unit of the biomarker diagnostic system of FIG. 1, according to an embodiment of the present invention.

With reference now to FIGS. 1, 2, and 7, the feedback unit 55, according to some embodiments, may be configured to output a signal 85 based on the physiological event prediction 80 as determined by the processor 30. The output 70 of the feedback unit 55 may be the same as the signal 85 that is output by the feedback unit 55; although for some embodiments the output 70 and the signal 85 may be two discrete types of output provided by the feedback unit 55. Accordingly, the physiological event prediction 80 may be output as the signal 85 by the feedback unit 55 in accordance with the output techniques described above with respect to the output 70. Furthermore, the signal 85 may be electrical, chemical, mechanical, optic, or magnetic in nature, or combinations thereof.

Figures 8A, 8B, 8C:
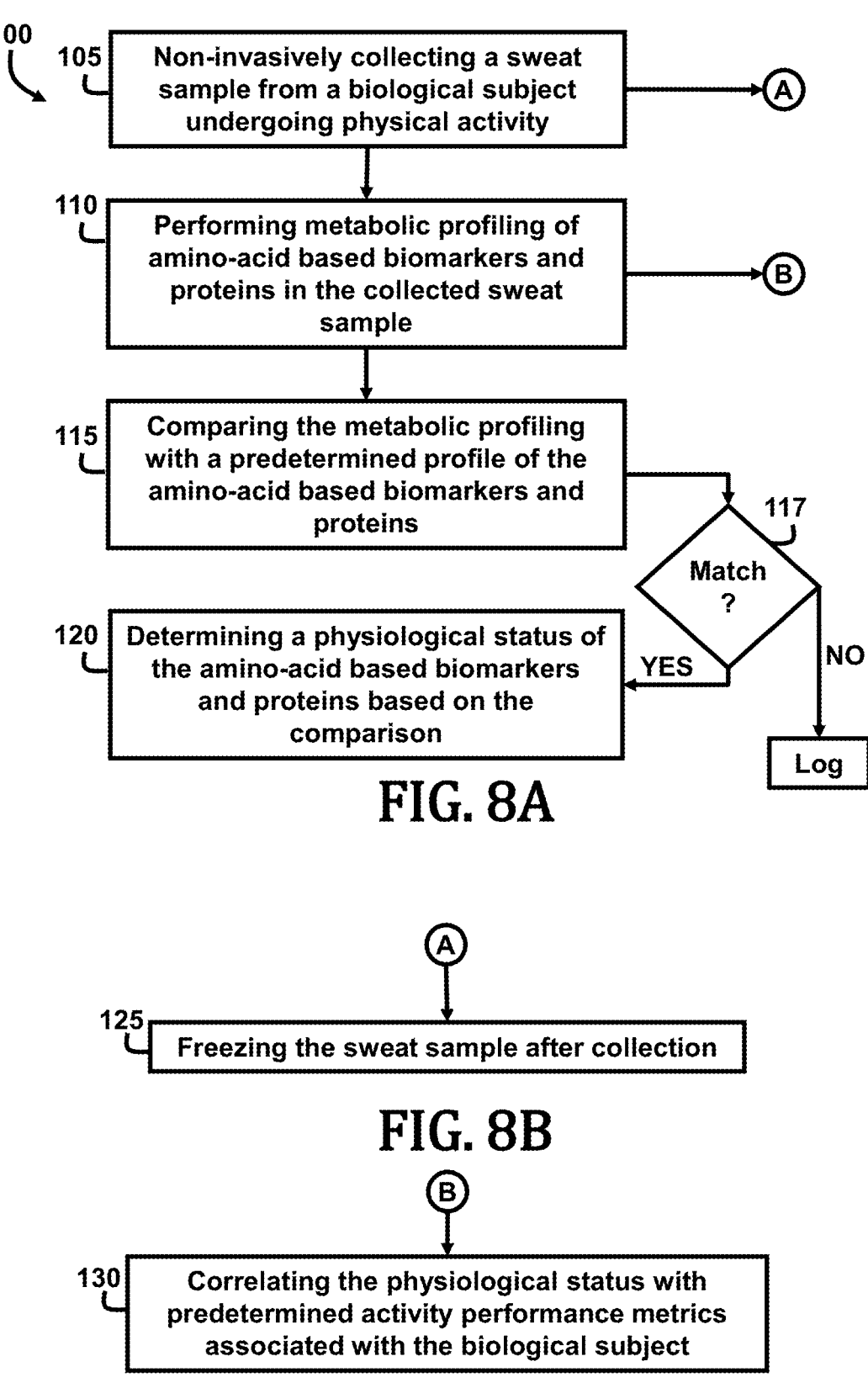
FIG. 8A is a flow diagram illustrating a diagnostic method according to an embodiment of the present invention.
FIG. 8B is a flow diagram illustrating a method of handling sweat samples in the method of FIG. 8A and in accordance with an embodiment of the present invention.
FIG. 8C is a flow diagram illustrating a method of processing in the method of FIG. 8A and in accordance with an embodiment of the present invention.

Referring now to FIGS. 1, 2, and 8A, a diagnostic method 100 in accordance with the embodiments herein is described. The method 100 begins with collecting a sweat sample 20, such as a non-invasive collection, from a biological subject 25 undergoing physical activity (Block 105). An amount or volume of the sweat sample 20 collected may be any suitable minimal amount or volume necessary to conduct diagnostic biological, chemical, or analytical testing thereon. The collection of the sweat sample 20 may occur using any suitable type of collection mechanism, one exemplary mechanism being MACRODUCT Sweat Collection devices (available from ELITechGroup Biomedical Systems, Logan, Utah, USA). The physical activity may be any type of exercise or other physical activity capable of causing the biological subject 25 to excrete the sweat sample 20.

A metabolic and/or proteomic profile 35 of biomarkers 40 in the collected sweat sample 20 may then be performed (Block 110). According to some embodiments, preforming the profile 35 may include retrieving of data from various biological/biochemical databases 42 to analyze the biomarkers 40 in the sweat sample 20. Additionally or alternatively, performing the profile 35 may include one or more diagnostic procedures, as further discussed in the examples described below.

The method 100 continues by comparing the profile 35 with a predetermined profile 45 of the biomarkers 40 (Block 115). According to some embodiments, the predetermined profile 45 may comprise a predetermined shift or change in protein/metabolite presence or abundance. For example, the detected biomarkers 40 in the sweat sample 20 may be compared with stored listing or catalogue of amino-acid based biomarkers and proteins in the predetermined profile 45 to determine whether a match exists. If a match exists ("YES" branch of Decision Block 117), then the method 100 may continue to determining a physiological status 50 of the biomarkers 40 based on the comparison (Block 120). If a match does not exist ("NO" branch of Decision Block 117), then a new biomarker and protein may be identified for addition to the predetermined profile 45 and suitably added to other biological, chemical, or analytical databases.

According to some embodiments, the physiological status 50 may describe a biomarker profile of the biomarkers 40. In another embodiment, the physiological status 50 may comprise metadata of the biological, chemical, or analytical signatures associated with the biomarkers 40. In still other embodiments, the physiological status 50 may comprise a computer-generated health assessment report identifying medical-related prognosis associated with the biological subject 25 based on an assessment of the particular combination of amino acids, proteins, and so forth comprising the biomarkers 40 present in the sweat sample 20. In one aspect of the embodiments herein, data normalization processing of the data associated with the biological, chemical, or analytical signatures of the biomarkers 40 may occur using any suitable data normalization technique or algorithm.

According to some embodiments, the sweat sample 20 may be frozen after collection (Block 125, FIG. 8B). Freezing permits the sweat sample 20 to be saved for diagnostic testing in a setting (location, time, or both) that is different from the setting of collection. The freezing process may include the use of liquid nitrogen or any other suitable freezing techniques and materials.

According to some embodiments, the physiological status 50 may include an identification of the biomarkers 40, an identification of diseases associated with the biomarkers 40, an identification of a health status of the biological subject 25 based on a metabolomic profile of the biomarkers 40 in the collected sweat sample 20, an identification of a health status of the biological subject 25 based on a proteomic profile of the biomarkers 40 in the collected sweat sample 20, or combinations thereof. Accordingly, the embodiments herein establish metabolomic and proteomic profiles of the sweat sample 20, which provides a basis for biomarker discovery efforts for human performance monitoring. Because of very low concentrations of endogenous metabolites present in sweat, metabolomic analysis of sweat with high coverage is difficult, making it less widely used for metabolomics research. Accordingly, the embodiments herein uniquely identify a number of proteins and amino acid-based biomarkers 40 in the sweat sample 20, such as proline, valine, threonine, leucine/isoleucine, and glutamic acid, among others. Changes in concentration profiles of these biomarkers are correlated to modified physiological states in the biological subject 25.

According to some embodiments, the physiological status 50 may be correlated with predetermined activity performance metrics (i.e., such as established by the data analytics assessment 75, for example) associated with the biological subject 25 (Block 130). The predetermined activity performance metrics provided by the data analytics assessment 75 may provide a health/medical assessment of the biological subject 25 based on predetermined health profiles and risk factors associated with a similar physiological status 50 preprogrammed and processed by the processor 30. For example, the predetermined activity performance metrics provided by the data analytics assessment 75 may assess whether the biological subject 25 is at risk of experiencing a particular physiological event (such as a heart attack, fainting, etc.) based on the physiological status 50. The data analytics assessment 75 may be based on real-time analysis of the sweat sample 20 (as in FIG. 4) and a continuous collection of sweat samples 20x (as in FIG. 5), for example. Detailed examples of the method are discussed in the example section, below.

And now, with reference to FIGS. 9A-9D, with continued reference to FIGS. 1 and 2), a system 200 for generating physiological performance data 60 in a computer 205 according to embodiments of the present invention is described. The computer 205 includes the processor 30 and a machine-readable storage medium 210. For some embodiments, the computer 205 may be part of any of the sensor 15, the processor 30, the feedback unit 30, or the wearable exercise-tracking device 65 attached to the biological subject 25. Alternatively, the computer 205 may be a standalone device or part of another electronic device or server system communicatively linked to any of the sensor 15, the processor 30, the feedback unit 55, or the wearable exercise-tracking device 65.

The processor 30 may include a central processing unit, microprocessors, microcontroller, hardware engines, and/or other hardware devices suitable for retrieval and execution of computer-executable instructions (illustrated with reference numbers ranging 215-255) stored in the machine-readable storage medium 210. The processor 30 may fetch, decode, and execute computer-executable instructions 215-255 to enable execution of locally hosted or remotely hosted applications for controlling action of the computer 205. Remotely hosted applications may be accessible on one or more remotely located devices, for example, communication device 260. For example, the communication device 260 may be a computer, tablet device, smartphone, or remote server. For some embodiments, the communication device 260 may comprise any of the sensor 15, the feedback unit 55, or the wearable exercise-tracking device 65. In alternative or addition to retrieving and executing instructions, the processor 30 may include one or more electronic circuits including a number of electronic components for performing the functionality of one or more of the instructions 215-255.

The machine-readable storage medium 210 may be any electronic, magnetic, optical, or other physical storage device that stores computer-executable instructions 215-255. Thus, the machine-readable storage medium 210 may be, for example, RAM, an Electrically-Erasable Programmable ROM, volatile memory, non-volatile memory, flash memory, a storage drive (e.g., a hard drive), a solid-state drive, optical drive, any type of storage disc (e.g., a compact disc, a DVD, etc.), and the like or combinations thereof. The machine-readable storage medium 210 may include a non-transitory computer-readable storage medium. The machine-readable storage medium 210 may be encoded with executable instructions for enabling execution of remotely hosted applications accessed on the one or more remotely located devices 260.

Figure 9A:
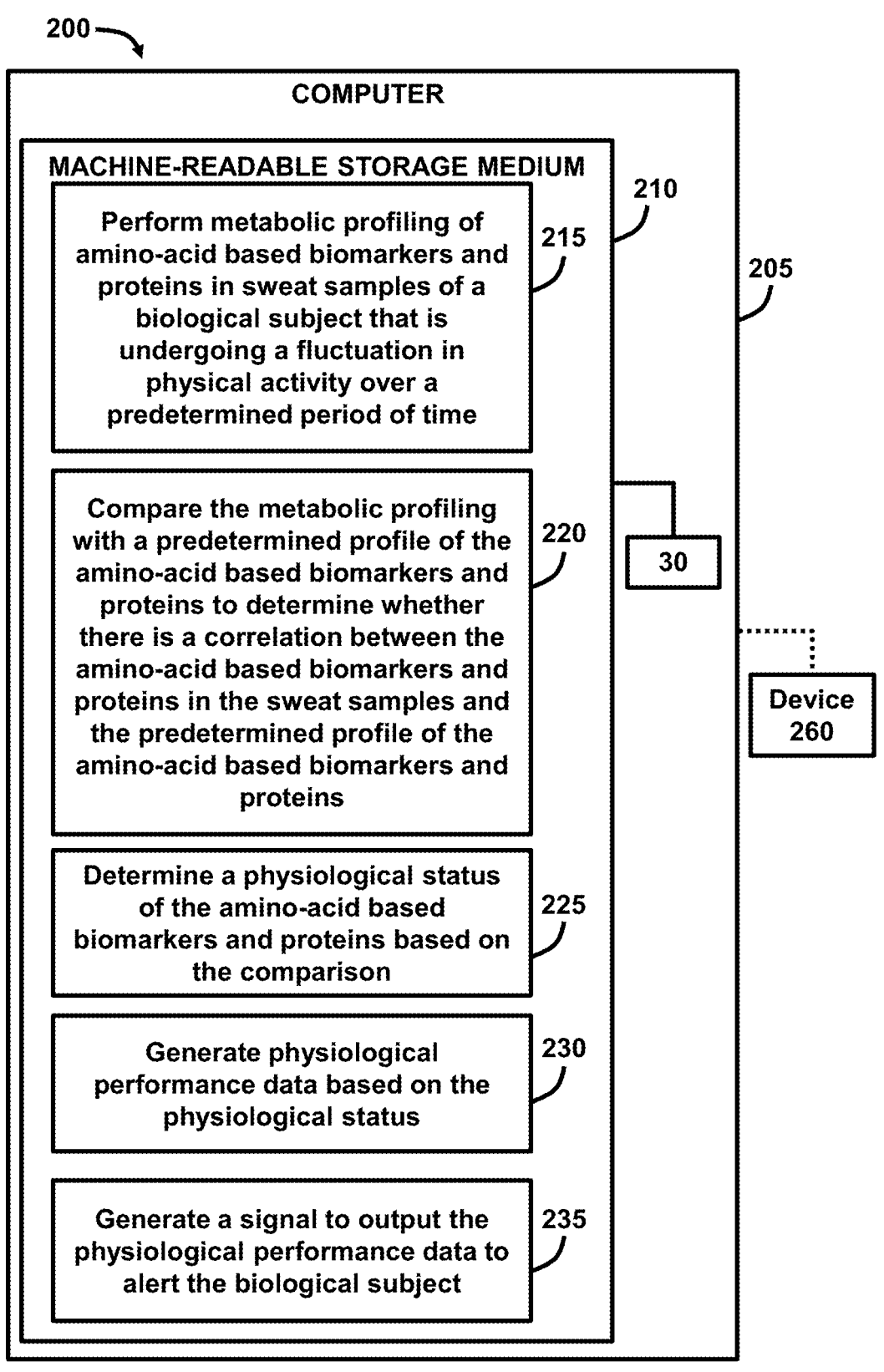
FIG. 9A is a block diagram illustrating a system to process biomarkers associated with sweat samples according to an embodiment of the present invention.

For some embodiments, the processor 30 of the computer 205 executes the computer-executable instructions 215-255. For example, as shown in FIG. 9A, Block 215 instructs the computer 205 to perform metabolic and proteomic profiling of biomarkers 40 in sweat samples 20x (FIG. 5) of the biological subject 25 that is undergoing a fluctuation in physical activity over a predetermined period of time. For example, the biological subject 25 may be exercising or undergoing any other type of physical activity that results in the excretion of the sweat samples 20x (FIG. 5). The predetermined period of time may be based on a set period of time or may be based on the level of activity of the biological subject 25 such that once the biological subject 25 is no longer excreting the sweat samples 20x (FIG. 5), then it may be determined that the predetermined period of time has concluded. According to some embodiments, the metabolic and proteomic profiling may involve retrieval of data from various biological/biochemical databases to analyze the biomarkers 40 in the sweat samples 20x (FIG. 5).

Block 220 instructs the computer 205 to compare the profile 35 with a predetermined profile 45 of the biomarkers 40 to determine whether there is a correlation between the biomarkers 40 in the sweat samples 20x (FIG. 5) and the predetermined profile 45 of the biomarkers 40. The predetermined profile 45 may include a predetermined shift in protein/metabolite abundance. If a correlation is identified, then Blok 225 instructs the computer 205 to determine a physiological status 50 of the biomarkers 40 based on the comparison a physiological status 50 of the biomarkers 40. If a correlation does not exist, then a new biomarker and protein may be identified for addition to the predetermined profile 45 and may suitably be added to other biological, chemical, and/or analytical databases. The physiological status 50 may describe a profile of the biomarkers 40; may comprise metadata of the biological, chemical, and/or analytical signatures associated with the biomarkers 40; or a computer-generated health assessment report identifying medical-related prognosis associated with the biological subject 25 based on an assessment of the combination of the biomarkers 40 present in the sweat samples 20x (FIG. 5). In one aspect of the embodiments herein, the data normalization processing of the data associated with the biological, chemical, and/or analytical signatures of the biomarkers 40 may occur using any suitable data normalization technique or algorithm.

Block 230 instructs the computer 205 to generate physiological performance data 60 based on the physiological status 50. For some embodiments, the physiological performance data 60 may be output as images, video, alphanumeric characters, and any other type of symbols that are displayed by the computer 205, the communication device 260, or both. In other embodiments, the physiological performance data 60 may be output as an audio signal that may include any type of sound, ringtone, music, computer-generated words or any suitable audio format that is stored as an audio file, for example, and capable of being processed by the processor 30 for output by the computer 205, communication device 260, or both. For still other embodiments, the physiological performance data 60 may be output as mechanical vibration caused by a motor (not shown) in the computer 205, the communication device 260, or both, that may be offset and weighted causing a vibration upon rotation. The processor 30 may determine that type of output of the physiological performance data 60 that is generated based on the physiological status 50 that is determined by the processor 30.

A combination of different types of output (i.e., audio, video, and/or vibration) may be output as the physiological performance data 60 according to other embodiments. The physiological performance data 60 may comprise any type of biometric data associated with the biological subject 25 and which is capable of being determined using an analysis of the sweat samples 20x (FIG. 5) such as the heart rate, pulse, etc. among other types of biometric data.

Block 235 instructs the computer 205 to generate a signal 85 to output 70 the physiological performance data 60 to alert the biological subject 25. The signal 85 may be output 70 by the computer 205, the communication device 260, or both. The output 70 of the computer 205, the communication device 260, or both may be the same as the signal 85 that is output by the computer 205, the communication device 260, or both. Alternatively, the output 70 may be separate and distinct from the signal 85. Accordingly, the signal 85 that is output by the computer 205, the communication device 260, or both may involve output techniques, as described above with respect to the output 70. Furthermore, the signal 85 may be any of an electrical, chemical, mechanical, optic, and magnetic signal, or combinations thereof.

As shown in FIG. 9B, Block 240 instructs the computer 205 to track a historical record of the physiological performance data 60 associated with the biological subject 25. The historical record may provide a health/medical history associated with the biological subject 25 based on the physiological performance data 60 and any updates or real-time changes to the physiological performance data 60. The tracking of the historical record may provide the biological subject 25 with a historical context of his/her state of health over a predetermined period-of-time to assess trends and so forth.

As shown in FIG. 9C, Block 245 instructs the computer 205 to compare the physiological performance data 60 with a predetermined list of physiological events. The predetermined list of physiological events may be stored in memory 47, which may be part of the computer 205 or communicatively linked thereto. The predetermined list of physiological events may provide various types of health-related events that the biological subject 25 may undergo, such as illnesses, diseases, or medical episodes (i.e., cardiac events, fainting, etc.), among others.

Block 250 instructs the computer 205 to generate a predicted physiological event for the biological subject 25 based on a correlation of the physiological performance data 60 with at least one physiological event from the predetermined list of physiological events. For example, the predicted physiological event that is generated for the biological subject 25 may include an assessment of the likelihood of the biological subject 25 experiencing a particular type of health-related event (i.e., a heart attack, fainting, etc.).

Figure 9D:
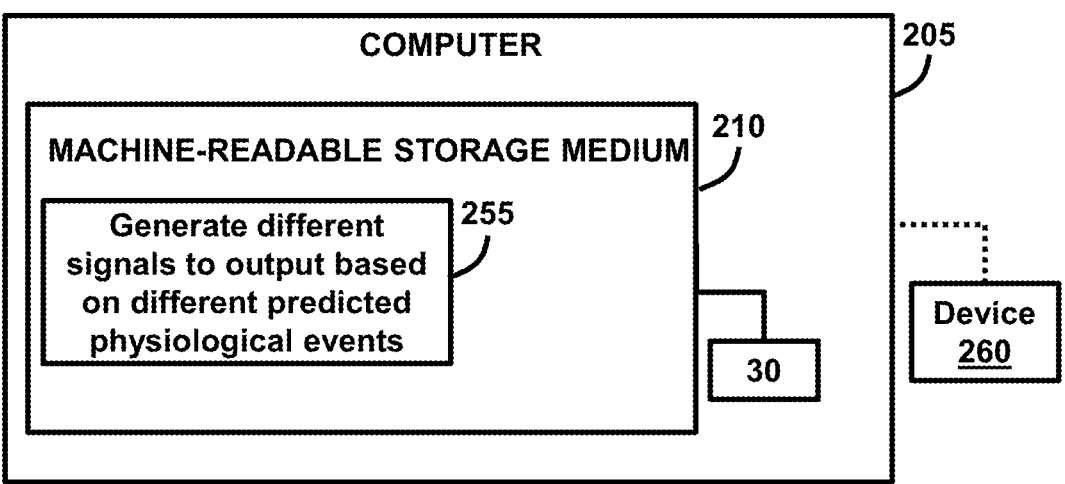
FIG. 9D is a block diagram illustrating a system to generate signals used with the processing of biomarkers associated with sweat samples, according to an embodiment of the present invention.

As shown in FIG. 9D, Block 255 instructs the computer 205 to generate different signals 85 to output based on different predicted physiological events. For example, the predicted physiological event that is generated for the biological subject 25 may be presented or alerted to the biological subject using any of an audio, video, image, and vibration signals 85. The type of signal 85 that is generated may be dependent on a category of the predicted physiological events. In this regard, for example, life-threatening predicted physiological events may include a combination of signals 85 to ensure that the biological subject 25 is apprised of a potential dangerous health-related situation.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Examples

The specific parameters, values, amounts, ranges, materials, types, brands, etc. described below are approximates or exemplary in nature and were merely selected for the experiment. As such, the embodiments of the present invention are not limited to the specific descriptions and examples below. To add support for the use of sweat as a non-invasive media for human performance monitoring, the techniques provided by the embodiments herein were experimentally verified using volunteer human participants ranging in age from 18 to 45 and having no current injury or illness. Generally, the participants were subjected to a physical exertion model using a treadmill. Following exercise, sweat was collected, aliquoted, and analyzed for metabolite and protein content via high-resolution mass spectrometry. Overall, proteomic analysis demonstrated significant enrichment steps are involved for proteomic biomarker discovery from single sweat samples as protein abundance is generally low in this media. Furthermore, the results indicated a potential for protein degradation, or a large number of low molecular weight protein/peptides, in these samples. Metabolomic analysis shows a strong correlation in the overall abundance among sweat metabolites. Additionally, hierarchical clustering of participant metabolite abundances demonstrates some trends emerging. Moreover, these data suggest with a greater number of biological replicates, stronger, statistically significant results, may be obtained. These data highlight several technical obstacles that had to be overcome of sweat analysis for biomarker discovery applications. Collectively, the experiment represents the first simultaneous use of both the proteomic and metabolomic analysis to investigate sweat, and the results support the validity of the embodiments herein demonstrating that sweat may hold proteomic and/or metabolomic biomarkers.

The experiment was conducted in a temperature and humidity-controlled laboratory setting (mean temperature of $22.20°$ C.$\pm0.15°$ C. and a mean humidity of 0.2% 0.0%). Participants took part in two experimental sessions (A and B) separated by at least two days. The order of the sessions was mixed and was completed based on participant availability. During session A participants completed a $VO_2$ max treadmill test using the well-known Bruce protocol. This was used to determine the participants' aerobic capacity, ventilatory threshold, and maximum heart rate (bpm). During session B participants were given a questionnaire to assess their regular exercise frequency and sleep duration. Participants were randomly assigned to one of three test conditions: low, moderate, and high intensity. The participants were equipped with sweat collection devices, as further described below, along with a heart rate monitor. All the participants wore a standard issue Airman Battle Uniform (ABU), and the heart rate monitor was placed under the ABU.

Prior to dawning the tactical gear, participants washed their forearms with running tap water for a time ranging, generally, from 5 sec to 10 sec, per arm and without soap. The air-dried forearms were then wiped with 70% isopropyl alcohol swabs until no visible residue was observed and air-dried. Eight adhesive-free MACRODUCT Sweat Collection devices (available from ELITechGroup Biomedical Systems, Logan, Utah, USA) were affixed to the patients' arm with VELCRO bands—that is, four devices per arm. Compression sleeves were placed over the collection devices to maintain device position and to induce (or increase) sweat production.

Following collection device placement, the participants dawned tactical gear, which was approximately 21.9 kg of standard issue United States Air Force (USAF) tactical gear, including a combat helmet (about 1.5 kg), a weighted rucksack (about 15.9 kg), body armor (about 4.5 kg), and a decommissioned M4 rifle. Once equipped, the participants marched on a treadmill until a state of physical exhaustion. Each participant had access to water throughout the march. Exhaustion was determined by each subject's own perception of an exhausted state. Throughout the controlled march, the heart rate was continuously monitored, and subjective measurements of perceived exertion were obtained using the well-known Borg Scale, every three minutes.

After completion of the treadmill march, excreted sweat was collected from each of the eight collectors, via transfer pipette, and pooled in a single 5 mL EPPENDORF LoBind tube on ice. The samples were immediately aliquoted, frozen on liquid nitrogen, and lyophilized overnight. Proteomic aliquots were supplemented with MS-Safe protease inhibitor cocktail (available from Sigma-Aldrich, St. Louis, Missouri, USA). All proteomic and metabolomic samples were stored at $-80°$ C. until analysis.

In-Solution Proteomics Sample Preparation

Lyophilized proteomic aliquots were resuspended in 75 μL water (OPTIMA MS Grade, available from Thermo Fisher Scientific, Waltham, Massachusetts, USA). 60 μg of each sample was diluted in 50 mM ammonium bicarbonate. A dithiothreitol (DTT, 5.6 mM at $95°$ C. for 5 min) reduction and an iodoacetamide (10 mM at ambient temperature for 20 min in the dark) alkylation was performed. 200 ng of sequencing grade-modified trysin was added and samples were incubated at $37°$ C. overnight with gentle shaking. 1 μL of formic acid was added to each sample and the samples were vacuum centrifuged to dryness. Samples were stored at $-80°$ C. until analysis. The samples were resuspended in a loading buffer (2% acetonitrile: 0.03% trifluoroacetic acid (TFA, aq)) and peptide concentration was estimated using a NANODROP spectrophotometer (available from Nano-Drop, Wilmington, Delaware, USA).

In-Gel Proteomics Sample Preparation

Two separate 14% sodium dodecyl sulfate polyacrylamide gel electrophoresis (SDS-PAGE) gels were run using either 175 μg of undigested pooled sweat peptides, based on a NANODROP peptide estimation, or 2 μg of undigested pooled sweat proteins, based on the well-known Bradford analysis. Proteins and peptides were fixed with 50% ethanol: 10% acetic acid for 1 hour. Gels were briefly washed with water and stained overnight with BIO-SAFE Coomassie (available from BioRad, Hercules, California, USA) at $4°$ C. The stain was removed with frequent washes with water and stored at $4°$ C. until digestion.

Gel bands, 13 slices from the 175 μg peptide gel and 16 slices from the 2 μg protein gel, were excised and soaked in 50% methanol: 5% acetic acid (aq) for 1 hr, twice. 200 μL of acetonitrile was added for 5 min and gel pieces were dried in a vacuum centrifuge. Gel pieces were reduced with dithiothreitol (DTT) (75 μL of 32.4 mM for 30 min at ambient temperature) and alkylated with iodoacetamide (75 μL of 81.1 mM for 30 min in the dark). Pieces were washed with 100 mM ammonium bicarbonate and dehydrated with acetonitrile twice. Acetonitrile was removed in a vacuum centrifuge and gel was rehydrated for 10 min with 50 μL of 20 ng/μL of sequencing grade-modified trypsin in 50 mM ammonium bicarbonate. Excess trypsin solution was removed, 20 μL of 50 mM ammonium bicarbonate was added, and samples were digested overnight at ambient temperature. Peptides were extracted by adding 30 μL of 50% acetonitrile: 5% formic acid (aq) twice for 10 min each. Peptides were concentrated to approximately 25 μL in a vacuum centrifuge. Samples were stored at $-80°$ C. until proteomic analysis.

Proteomics Liquid Chromatography Mass Spectrometry (LC-MS/MS)

2 μg of in-solution samples or 6 μL of in-gel samples were injected onto a 3 μm, 200 Å PRONTOSIL C18AQ trap column (available from nanoLCMS Solutions, Rancho Cordova, California, USA) using a DIONEX ULTIMATE 3000 RSLCnano (available from Thermo Fisher Scientific) operated in an online desalting configuration. Peptide trapping and washing was performed isocratically using loading buffer at 5 μL/min for 5 min. Reverse phase nano separations were performed on an EASY-SPRAY PepMap (available from Thermo Fisher Scientific) 2 μm, 50 μm×150 μm, 100 Å column at 250 nL/min. Mobile phase A was comprised of 0.1% formic acid (aq) and mobile phase B was comprised of 0.1% formic acid in acetonitrile (OPTIMA MS Grade).

The 180 min analytical separation was as follows: 2% B for 5 min, a linear increase to 40% B at 163 min, 98% B wash from 165 min to 168 min, and equilibration at 2% B from 170 min to 180 min. Analytical eluent was introduced via EASY-SPRAY source (2.5 kV) into an LTQ ORBITRAP XL mass spectrometer operated in top 6 data dependent mode (available from Thermo Fisher Scientific). $MS^1$ scans were obtained in the LTQ ORBITRAP XL mass spectrometer at 30,000 resolution across 350-2000 m/z. MS' scans were performed in the ion trap with fragmentation occurring at 35% normalized collision energy. Dynamic exclusion settings were as follows: repeat count 3, repeat duration 30, and exclusion duration 60. In-gel samples were run under the same LC and MS conditions except analytical separations were across a 45 min linear 2% B to 40% B gradient (64 min total separation).

Immunoblotting

SDS-Page gels were run as described above in the in-gel proteomics sample preparation section. Gel proteins were transferred to nitrocellulose, Ponceau S stained, and blotted for sweat proteins. Chemiluminescent detection was performed using either the Pico or Fempto substrate (available from Thermo Fisher Scientific) and a GE IMAGEQUANT RT ECL imager (available from GE, Pittsburgh, Pennsylvania, USA).

Metabolomic Hydrophilic Interaction Liquid Chromatography-Mass Spectrometry (HILIC-MS) Analysis Lyophilized sweat samples were reconstituted to aliquoted volume in 50% acetonitrile supplemented with 25 nmil isotopically labeled Metabolomics Amino Acid Mix Standard (available from Cambridge Isotope Laboratories, Tewksbury, Massachusetts, USA). Samples were run in a randomized order using a standard spreadsheet software program (such as EXCEL v.14.7.7, available from Microsoft Corporation, Redmond, Washington, USA).

Polar sweat compounds and amino acid calibration curves were separated on a Phenomenex LUNA HILIC column (3 μm, 200 Å, 100 mm×3 mm, available from Phenomenex, Torrance, California, USA) and a DIONEX ULTIMATE 3000 RSLCnano (available from Thermo Fisher Scientific) utilizing the micropump at 40° C. Mobile phase A contained 0.01 M ammonium formate (>99.0%, available from Sigma-Aldrich, St. Louis, Missouri, USA) in 4.5% acetonitrile (aq) at pH 3.0 while mobile phase B contained 0.01 M ammonium formate in 95% acetonitrile (aq) at pH 3.0. Injections (2 μL) were subjected to the following gradient at 500 μL/min: 0 min to 3 min hold at 97% B, 3 min to 9 min 65% B, 9 min to 9.5 min 50% B for one minute, 10.5 min to 11.5 min 97% B and hold for 10 min at 97% B. Either a step gradient or a linear gradient could be used. Eluent was introduced into an LTQ ORBITRAP XL mass spectrometer (available from Thermo Fisher Scientific) setup for LC-MS affixed with a heated electrospray ionization source. For positive mode, the source and LTQ ORBITRAP XL mass spectrometer were operated with the following parameters: source voltage 4.5 kV, sheath gas 8, aux gas 1, capillary temperature 275° C., and scans were made from 60-550 m/z at 7500 resolution. For negative mode, the source and LTQ ORBITRAP XL mass spectrometer were operated with the following parameters: source voltage 4.5 kV, sheath gas 5, capillary temperature 280° C., and scans were made from 100-550 m/z at 7500 resolution. The MS system was calibrated and tuned prior to each ionization mode sample run.

Data Processing—Proteomics

Proteomic analysis was performed using the MassMatrix database search engine (v. 2.4.2). Tandem data was searched against the Uniprot complete *H. sapien* proteome supplemented with the cRAP contaminant database using an $MS^1$ mass tolerance of 10 ppm, an $MS^n$ tolerance of 0.8 Da, and three allowed missed tryptic cleaves. The false discovery rate (FDR) was estimated using a reversed sequence database. Protein groups were required to have less than 5% FDR, 2 unique peptide matches to be retained in the analysis. The keratin and cRAP protein groups were removed from the analysis as contaminants. Gene ontology information, protein class, molecular function, biological process, and cellular component for identified protein groups were tabulated using the Panther Classification System (v.13.1).

Data Processing—Metabolomics

Positive and negative metabolomics raw data files were uploaded to the XCMS Online Software Suite as a single batch for retention time alignment and feature detection. The feature SCMS settings were as follows: centWave detection with 10 ppm mass tolerance and 5-30 s peak width, 1 m/z orbiwarp retention time correction, and alignment bandwidth of 5 s. Feature lists and abundances (161 features positive mode, 133 features negative mode) were exported for further statistical analysis.

The XCMS feature list was manually searched, for $M+1^+$ or $M-1^-$ ions, against the Metlin Database as a 5 ppm mass accuracy using the simple search feature. Neat standards were ordered for the resulting tentative compound identifications. Confirmatory analyses for MS/MS were performed using the HILIC methods described above. Standards and stored sample aliquots were detected in MS/MS mode on an ORBITRAP FUSION LUMOS TRIBRID mass spectrometer (available from Thermo Fisher Scientific). The ORBITRAP FUSION LUMOS TRIBRID mass spectrometer was operated under the following conditions. For positive mode, source voltage 3.8 kV, sheath gas 5.45, aux gas 2, sweep gas 3, capillary temperature 300° C., and MS' scans were obtained at 60,000 resolution across a 60-300 m/z range. A mass list corresponding to neat standard m/z values was entered and fragments were generated for the mass list (±10 ppm) using collision-induced dissociation (CID) at 10%, 20%, and 40% normalized collision energy (10 ms activation) within the ion trap. $MS^2$ detection of fragment ions was performed in the ORBITRAP FUSION LUMOS TRIBRID mass spectrometer with 7,500 resolution and a 50-300 m/z scan range over 3 microscans. For negative mode, source voltage 3.4 kV, sheath gas 15, sweep gas 1, capillary temperature 300° C., and MS' scans were obtained at 60,000 resolution across a 115-300 m/z range. A mass list corresponding to neat standard m/z values was entered and fragments were generated for the mass list and detected as described above.

All standard and sample MS/MS data were manually inspected and searched against the Metlin Database, as described previously, for mass accuracy and fragmentation patterns. Retention times of standards were tabulated using the XCALIBUR Qual browser software (available from Thermo Fischer Scientific) and compared to the experimental results. Metabolomic gene ontology terms for primary process, biological role, and industrial application were compiled from The Human Metabolome Database.

Statistical Analysis

Basic statistical analysis was performed using the Prism GRAPHPAD software (v. 5.0c, available from GraphPad Software Inc., La Jolla, California, USA). Additional statistical analysis was performed using the R statistical software (v.3.4.4). Metabolite abundance values were quantile normalized to account for technical variation between samples run on LC-MS systems at different times. Hierarchical clustering was performed on the correlation matrix of the metabolite compounds using average linkage. The resulting dendrogram was used to reorder the correlation matrix, placing most similar metabolites near one another and more dissimilar ones farther apart. The reordered correlation matric was visualized with a heatmap. Similarly, the subjects were clustered based on their metabolite profiles and reordered. Generalized linear model regression analysis with LASSO regularization was performed using the glmnet R packet.

Proteomic Analysis

Historically, the proteomic analysis of sweat has yielded a wide range of protein identifications, between 95 and 861. The stark difference in number of identifications among these previous studies is likely due to many methodological factors, such as collection, sampling locations on the body, sweat stimulation procedures, sample handling, and pooling. For biomarker discover efforts, a single sample from an individual must be able to be analyzed; i.e., no pooling, with minimal preparation steps to maintain large-scale through-put. Therefore, this approach was applied to single forearm sweat samples collected from participants marching on a treadmill. Data from in-solution tryptic digestion followed by a bottom-up shotgun proteomics illustrates a low number of protein groups identified from sweat via in-solution digestion: Dermcidin, Prolactin-inducible protein, Zinc-al-pha-2-glycoprotein, Serum albumin, Secretoglobin family 1D member 2, Calcium-transporting ATPase type 2C mem-ber 2, Mucin-like protein 1, 1 g kappa chain C region, Clusterin, and Desmoglein-1. The low number of groups identified from individual replicates suggests additional pro-tein enrichment steps may improve the overall depth obtained from a single sample. To further support the assertion that low abundance of proteins in sweat contributes to the low numbers of proteomic identifications, an in-gel tryptic digestion of pooled samples, 175 µg peptide load and 2 µg protein load, showed an increase in the protein groups identified (e.g., 80 protein groups). Select protein identifi-cations were verified by immunoblot. Inspection of the combined protein groups (82), identified from both the in-solution and the in-gel analyses, suggest 96% (79/82) of the data set was previously reported in the literature. While only a few novel protein groups were identified (3), these results suggest the protein groups in the present experiment highlight that the more abundant proteins in sweat may be utilized for biomarker discovery. Collectively, these results suggest single replicate sweat samples are too dilute to allow for biomarker discovery without additional sample prepa-ration strategies to enrich low abundant proteins.

Figure 10A:
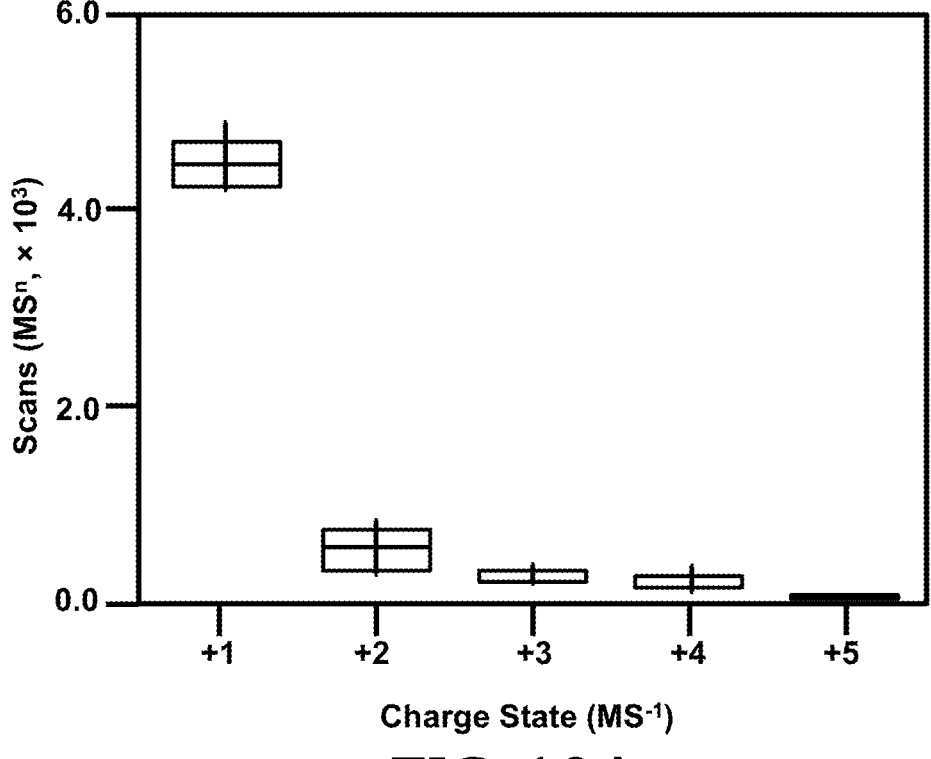
FIG. 10A is a graph illustrating a box-whisker plot of the number of MS$^1$ charge states selected for MS$^4$ scans, according to an embodiment of the present invention.
Figure 10B:
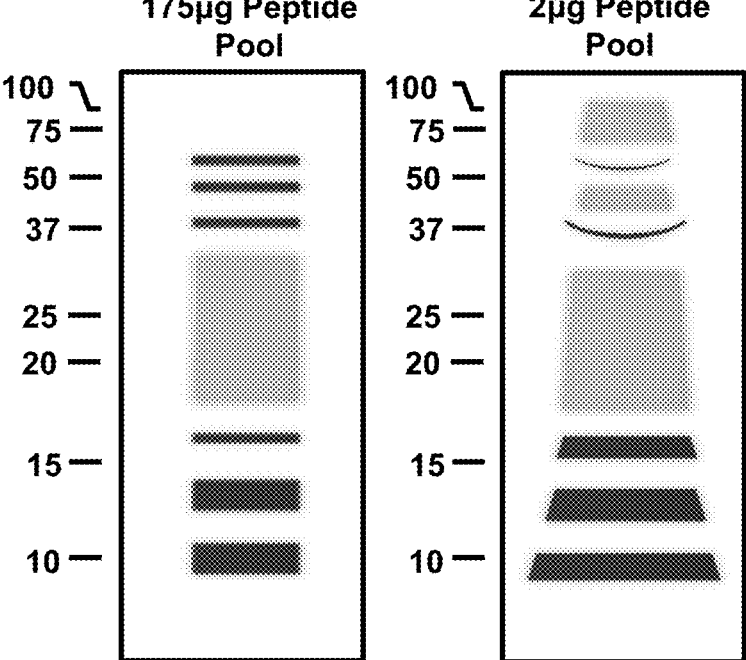
FIG. 10B is a diagram illustrating representative images of Coomassie stained gels from 175 µg peptide and 2 µg protein loading, according to an embodiment of the present invention.

Several additional factors beyond low protein concentra-tion may contribute to the small number of protein groups identified via the single replicate in-solution approach. First, inspection of the raw data suggests a large number of singly (+1) charged peptides were selected for MS$^n$ fragmentation, as shown in FIG. 10A. While singly charged peptides were not excluded in the method for fragmentation, the fragments of +1 peptide ions do not generate both b and y ions, which may lead to difficulty in confident spectral assignment with proteomic search engines. Next, SDS-PAGE gels of pooled, 175 µg sweat peptides or 2 µg sweat proteins, samples show a large group of low molecular weight (less than 17 kD) proteins or peptides are present in the excreted sweat as indicated in FIG. 10B. Generally, tryptic digests of low molecular weight proteins and peptides provide few unique peptide ions for confident protein assignment. Generally, tryptic digests of low molecular weight proteins and pep-tides provide few unique peptide ions for confident protein assignment. These results would support utilization of middle-down or top-down approaches to characterize this group of proteins. Next, inspection of the protein class and molecular gene ontology data illustrates the majority (53%) of the proteins fall into the hydrolase and enzyme modulator classes and 45% have catalytic activity molecular function as indicated in Tables 2 and 3, below. Taken together, the combination of singly charged peptides; i.e., non-specific cleavage, low molecular weight proteins/peptides within the samples, and the high abundance of enzymatic protein classes suggests proteolytic degradation may be present.

TABLE 2

| PROTEIN CLASS | |
| --- | --- |
| Protein Class | Percentage |
| Hydrolase | 29 |
| Enzyme Modulator | 24 |
| Signaling | 6 |
| Calcium Binding | 6 |
| Transfer/Carrier | 5 |
| Cell Junction | 5 |
| Oxidoreductase | 5 |
| Cell Adhesion | 5 |
| Nucleic Acid Binding | 5 |
| Defense/Immunity | 3 |
| Receptor | 3 |
| Membrane Traffic | 2 |
| Transcription Factor | 2 |
| Isomerase | 2 |
| Extracellular Matrix | 2 |
| Cytoskeletal | 2 |
| Transporter | 2 |
| Transferase | 2 |

TABLE 3

| MOLECULAR FUNCTION | |
| --- | --- |
| Function | Percentage |
| Catalytic Activity | 45 |
| Binding | 41 |
| Antioxidant Activity | 6 |
| Transporter Activity | 4 |
| Structural Molecule Activity | 4 |
| Receptor Activity | 4 |

Metabolomic Analysis of Sweat

Similar to sweat proteomics, the metabolomic analysis of sweat has yielded a relatively small number of metabolite identifications in the literature when compared to other media sources. Additionally, these metabolomic studies, as with the proteomic studies, utilize a diverse group of meth-ods for collection, sweat stimulation, sample handling, and analysis. Previous studies have illustrated a large group of polar metabolites, such as amino acids, are the predominant small molecules in this fluid. Therefore, an untargeted metabolomics approach, using hydrophilic interaction liquid chromatograph (HILIC) separations in combination with high-resolution MS detection, was applied to determine the polar metabolomic content of single sweat samples for biomarker discovery. Table 4, below, shows a list of the compounds tentatively identified from single sweat samples by both positive and negative ionization modes. To verify the tentative identity of the compounds, neat standards were obtained and run for comparison of retention time and MS' fragmentation patterns. Twenty-nine of the 48 tentative identifications (60%) were verified by retention time and/or MS/MS fragmentation. Of the 48 compounds tentatively identified, 81% (39/48) had been previously reported in the literature. These results establish that the metabolomics approach utilized in accordance with the embodiments herein is in line with historical metabolomic analysis sug-gesting these are the primary metabolite targets for bio-marker discovery in this media.

Approximately 60% of the tentatively identified com-pounds were verified by retention time and/or MS/MS fragmentation. It is considered that the tentative identifications that do not match the retention time with the neat standards may be a result of a matrix effect, such as salt content, of sweat compared to that of standards prepared in neat solutions. For example, all of the tentatively identified compounds that do not match the retention time of the neat 5 standards do so with increased observed retention times. Increases of salt content in HILIC separations generally provide greater retention; however, it appears as though it may be analyte and salt dependent. Therefore, it is plausible that a matrix effect may contribute to the lack of retention 10 time similarity among several of the tentatively identified compounds.

To identify the potential biological role and biological process associated with the metabolites identified, gene ontology terms were compiled from the Human Metabolome Database. Tables 5 and 6, below, illustrate the largest biological role grouping is essential and semi-essential amino acids (28%) and the predominant biological process represented is amino acid metabolism or degradation (26%). These results support previous evidence suggesting amino acids are the most abundant metabolites in sweat.

To determine how metabolite abundances vary together, a hierarchical cluster analysis was performed, which demonstrated a strong correlation existing among metabolite expression profiles. The results indicate a relationship among metabolite abundances in sweat, namely, amino acids are the primary polar metabolites present in sweat with their expression correlated among each other.

TABLE 4

SUMMARY OF THE METABOLITES IDENTIFIED FROM SWEAT

| Compound | CAS, Metlin ID, HMDB | m/z med | RT med (min) | Precursor Δ Mass (ppm) | Adduct | Fragments |
|---|---|---|---|---|---|---|
| Urocanic Acid | 104-98-3, 298, HMDB0000301 | 139.0499 | 1.11 | 2 | [M + H]+ | 121.0398, 95.0605 |
| Creatinine | 60-27-5, 8, HMDB0000562 | 137.0363 114.0659 | 1.13 1.14 | 4 2 | [M − H]− [M + H]+ | 93.0457 86.0961 |
| Choline | 62-49-7, 56, HMDB0000097 | 104.1067 | 1.30 | 3 | [M + H]+ | 60.0808, 58.0647 |
| Trolamine | 102-71-6, 43365, HMDB0032538 | 150.1121 | 1.42 | 2 | [M + H]+ | 132.1019, 114.0917 |
| Dimethylethanoiamine | 108-01-0, 88280, HMDB0032231 | 90.0911 | 1.48 | 3 | [M + H]+ | 72.0810 |
| L-Ascorbic Acid | 50-81-7, 249, HMDB0000044 | 175.0253 | 1.74 | 2 | [M − H]− | — |
| Diolamine | 111-42-2, 3239, HMDB0004437 | 106.0859 | 2.20 | 2 | [M + H]+ | 88.0758, 70.0648 |
| Taurine | 107-35-7, 31, HMDB0000251 | 126.0216 124.0079 | 2.28 2.27 | 2 4 | [M + H]+ [M − H]− | — 79.9567 |
| N-Acetyl-DL-Serine | 94-14-3, 96376, HMDB0002931 | 146.0464 | 2.42 | 3 | [M − H]− | 74.0245 |
| Uric Acid | 69-93-2, 88, HMDB0000289 | 167.0215 | 2.60 | 2 | [M − H]− | 124.0149, 96.0201 |
| L-Prolinamide | 7531-52-4, 73355 | 115.0862 | 2.61 | 3 | [M + H]+ | 70.0653 |
| L-Phenylalanine | 63-91-2, 28, HMDB0000159 | 166.0860 | 2.87 | 1 | [M + H]+ | 120.0808 |
| L-Leucine, | 61-90-5, 24, HMDB0000687 | 132.1016 | 2.90 | 2 | [M + H]+ | 86.0966, |
| L-Isoleucine | 73-32-5, 23, HMDB0000172 | | | | | 69.0692 |
| Pyrogultamic Acid | 98-79-3, 3251, HMDB0000267 | 128.0359 | 2.97 | 4 | [M − H]− | 82.0294 |
| Piperidine | 110-89-4, 64457, HMDB0034301 | 86.0962 | 2.99 | 2 | [M + H]+ | — |
| L-Methionine | 63-68-3, 26 HMDB0000696 | 150.0581 | 3.38 | 1 | [M + H]+ | 133.0308, 104.0518 |
| 3-Indoleacrylic acid | 1204-06-4, 5702, HMDB0000734 | 188.0703 | 3.60 | 1 | [M + H]+ | — |
| L-Tryptophan | 73-22-3, 33, HMDB0000929 | 205.0969 | 3.60 | 1 | [M + H]+ | 188.0705 |
| Pyrrolidine | 123-75-1, 87832, HMDB0031641 | 72.0805 | 3.65 | 3 | [M + H]+ | — |
| L-Valine | 72-18-4, 35, HMDB0000883 | 118.0860 | 3.65 | 2 | [M + H]+ | 72.0809, 55.0539 |
| L-Proline | 147-85-3, 29, HMDB0000162 | 116.0703 | 3.70 | 2 | [M + H]+ | 70.0653 |
| L-Tyrosine | 60-18-4, 34, HMDB0000158 | 182.0808 | 4.21 | 1 | [M + H]+ | 165.0547, 136.0757 |
| 5-Aminopentanoic acid | 660-88-8, 6902, HMDB0003355 | 118.0859 | 4.57 | 2 | [M + H]+ | 101.0831 |
| L-Carnitine | 541-15-1, 52, HMDB0000062 | 162.1121 | 5.41 | 2 | [M + H]+ | — |
| L-Alanine | 56-41-7, 11, HMDB0000161 | 90.0547 | 5.45 | 2 | [M + H]+ | — |
| Creatine | 57-00-1, 7, HMDB0000064 | 132.0764 | 5.75 | 2 | [M + H]+ | 90.0551 |
| L-Serine | 56-45-1, 30 HMDB0000187 | 106.0495 | 5.77 | 3 | [M + H]+ | 88.0395, 60.0455 |

TABLE 4-continued

SUMMARY OF THE METABOLITES IDENTIFIED FROM SWEAT

| Compound | CAS, Metlin ID, HMDB | m/z med | RT med (min) | Precursor Δ Mass (ppm) | Adduct | Fragments |
|---|---|---|---|---|---|---|
| L-Asparagnine | 70-47-3, 14, HMDR0000168 | 104.0358 | 5.83 | 4 | [M − H]⁻ | — |
| | | 133.0605 | 5.77 | 2 | [M + H]⁺ | — |
| | | 131.0468 | 5.83 | 4 | [M − H]⁻ | 113.0366 |
| L-Glutamine | 56-85-9, 18, HMDB0000641 | 147.0767 | 5.81 | 1 | [M + H]⁺ | — |
| Glycine | 56-40-6, 20, HMDB0000123 | 76.0391 | 5.92 | 2 | [M + H]⁺ | — |
| 5-Hydroxyectoine | 165542-15-4, 63420 | 159.0761 | 6.31 | 2 | [M + H]⁺ | 141.0649, 113.0712 |
| Citrulline | 372-75-8, 16, HMDB0000904 | 176.1027 | 3.31 | 1 | [M + H]⁺ | 159.0765, 113.0712 |
| | | 174.0890 | 6.34 | 3 | [M − H]⁻ | 131.0825 |
| L-Glutamate | 58-86-0, 19, HMDB0000148 | 148.0601 | 6.45 | 2 | [M + H]⁺ | 130.0502, 84.0437 |
| L-Histidine | 71-00-1, 21, HMDB0000177 | 156.0765 | 6.52 | 1 | [M + H]⁺ | 110.0715, 83.0604 |
| | | 154.0627 | 6.55 | 3 | [M − H]⁻ | 137.0352, 93.0452 |
| L-Aspartic Acid | 56-84-8, 15, HMDB0000191 | 132.0307 | 6.62 | 3 | [M − H]⁻ | 115.0035, 88.0402 |
| L-Arginine | 74-79-3, 13, HMDB0000517 | 175.1186 | 7.22 | 2 | [M + H]⁺ | 70.0654, 60.0558 |
| | | 173.1048 | 7.22 | 2 | [M − H]⁻ | 131.0824 |
| L-Lysine | 56-87-1, 25, HMDB0000182 | 147.1125 | 7.36 | 2 | [M + H]⁺ | — |
| L-Pipecolic acid | 3105-95-1, 6310 HMDB0000716 | 130.0859 | 7.36 | 2 | [M + H]⁺ | — |
| | | 133.0968 | 7.42 | 2 | [M + H]⁺ | — |
| Ornithine | 70-26-8, 27, HMDB0000214 | 131.0831 | 6.34 | 3 | [M − H]⁻ | 113.0366, 85.0658 |
| L-Prolinemide | 7531-52-4, 73355 | 115.0862 | 7.43 | 3 | [M + H]⁺ | — |

TABLE 5

BIOLOGICAL ROLE FOR METABOLITES IDENTIFIED FROM SWEAT SAMPLES

| Biological Role | Percentage |
|---|---|
| Essential, Semi-essential Amino Acid | 26 |
| Trace Element | 23 |
| Essential Vitamin, Vitamin or Nutrient | 10 |
| Metabolite | 10 |
| Drug Metabolite | 6 |
| Waste Product | 6 |
| Free Radical Scavenger | 3 |
| Antioxidant | 3 |
| Neurotransmitter | 3 |
| Osmolyte | 2 |
| Energy Source | 2 |
| Anticonvulsant | 2 |
| RNA Component | 2 |

TABLE 6

BIOLOGICAL PROCESS FOR METABOLITES IDENTIFIED FROM SWEAT SAMPLES

| Biological Process | Percentage |
|---|---|
| Amino Acid Metabolism or Degradation | 26 |
| Miscellaneous Metabolism | 11 |
| Transcription/Translation | 11 |
| Peroxisome | 7 |
| Ammonia Recycling | 6 |
| Urea Cycle | 6 |
| Miscellaneous Biosynthesis | 5 |
| Miscellaneous Action Pathway | 5 |
| Purine Metabolism | 4 |

TABLE 6-continued

BIOLOGICAL PROCESS FOR METABOLITES IDENTIFIED FROM SWEAT SAMPLES

| Biological Process | Percentage |
|---|---|
| Carnitine Synthesis | 4 |
| Hypoacetylaspartia | 3 |
| Lysinuric Protein Intolerance | 3 |
| Pyridoxine Dependency | 2 |
| Catacholamine Biosynthesis | 2 |
| Fatty Acid Oxidation | 2 |
| Lysosome | 1 |
| Warburg Effect | 1 |

The embodiments herein represent the first technique that simultaneously investigates both proteomics and metabolomics from the same sweat samples. Collective examination of both data sets suggests the major protein groups identified have hydrolase and catalytic activity while amino acids remain the most abundant metabolites in sweat. Assuming hydrolase and catalytic degradation of proteins in sweat produce free amino acids lends further support to protein degradation leading to increases in free amino acids in sweat. This consideration is further strengthened by the strong relationship in expression of the metabolites, including amino acids, in sweat. If protein degradation were the source of amino acids in sweat, it would be expected that these metabolites would trend with exercise duration; i.e., longer time for enzymes to react with proteins to make free amino acids. Experimentally, it was recognized that some of the participants yielded an increase in amino acids during a long duration of exercise, while other participants yielded a decrease in amino acids during a long duration of exercise.

Additionally, no statistically significant result was found between the metabolite abundances and physiological or march parameters.

The experimental data suggests a confounding factor or factors may exist in the metabolomics data. First, one analytical result not presented in the experiment is localized sweat rate. Accurately estimating localized sweat rate is extremely difficult to achieve in practice. Gravimetric sweat rates, via filter paper or syringe mass changes are the most frequently used method for localized sweat rate estimation. However, this method fails to take into account the latent time to initiate sweat production, which may be different depending on the individual, leading to inaccurate estimates of collection times. Additionally, these methods ignore the excess sweat volume from saturated collection devices or incomplete recovery of sweat from within a collection pouch, yielding additional in total volume.

Next, the collection methodology used in the experiment may have contributed to some variability in the observed data set. For example, the Macroduct collection apparatus used in the experiment holds approximately 80 µL of sweat. This volume was generally below the amount of sweat each participant yielded suggesting an overflow of sweat out of the collector and lost. Therefore, the samples represent only the final portion of the exercise rather than a representation of the entire exercise. This factor may also have played a part in the confounding results for duration and metabolite abundance.

Moreover, while the arms of the participants were cleaned with water and isopropyl alcohol wipes, many compounds have links to industrial applications. For example, 54% (19/35) of the metabolites have been linked to personal care products. Furthermore, 60% (21/35) of the metabolites belong to the Food and Nutrition category. These results suggest further definition of the contribution of skin cosmetics/cleanliness and overall diet may be considered for further biomarker discovery from sweat.

Overall proteomic and metabolomic discovery from sweat yields some novel identifications. However, enrichment methodologies should be optimized to concentrate low abundant protein analytes from single sweat samples. Moreover, the definition of sample degradation and contamination should be outlined for proper metabolomics analysis from sweat.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Those skilled in the art will recognize that the embodiments herein can be practiced with modification within the spirit and scope of the appended claims.

Embodiments of the present invention, its various features and the advantageous details thereof, are explained more fully with reference to the non-limiting embodiments that are illustrated in the accompanying drawings and detailed in the following description. Descriptions of well-known components and processing techniques are omitted to not unnecessarily obscure what is being disclosed. Examples may be provided and when so provided are intended merely to facilitate an understanding of the ways in which the invention may be practiced and to further enable those of skill in the art to practice its various embodiments. Accordingly, examples should not be construed as limiting the scope of what is disclosed and otherwise claimed.

As described above, the ability to non-invasively monitor changes in personal physiology for detrimental conditions, such as hydration or fatigue, is becoming necessary to ensure safety in a number of job duties. However, only a few monitoring modalities, such as urine specific gravity for hydration, are available to monitor human performance non-invasively. Recent advancements in wearable technologies have pushed sweat into the forefront of human performance sensing and monitoring.

Accordingly, as the push intensifies to develop wearable electronics for real-time physiological and performance-based monitoring, sweat offers an extremely attractive matrix for continuous non-invasive sample collection to fit this need. Accordingly, sweat provides a unique opportunity for biomarker discovery research. Establishing a link between sweat analytes and human performance can facilitate a better understanding of the mechanisms through which analytes influence and/or reflect the outcomes of performance. Furthermore, this information may allow for building predictive models of performance through which analyte abundance can be turned into actionable information via feedback.

Embodiments of the present invention described herein provide a technique to identify novel small molecules and proteins associated with sweat and exercise to non-invasively monitor changes in personal physiology. The embodiments herein establish the proteomic and metabolomic profiles of sweat, providing a basis for biomarker discovery efforts for human performance monitoring. Because of very low concentrations of endogenous metabolites present in sweat, metabolomic analysis of sweat with high coverage is difficult, making it less widely used for metabolomics research. Accordingly, the embodiments herein uniquely identify a number of proteins, and amino-acid based biomarkers in sweat, such as proline, valine, threonine, leucine/isoleucine and glutamic acid. Changes in concentration profiles of these biomarkers are correlated to modified physiological states in subjects. The technique provided by the embodiments herein involves (i) collecting sweat as frozen lyophilized samples, (ii) establishing biomarker identifications by performing metabolic and proteomic profiling of small molecules and proteins in the samples, and (iii) quantitation to determine the physiological status of the molecules/proteins to establish any diseases, establish an identification profile, and a metabolomic profile of the subject. Moreover, the embodiments herein provide for the ability to monitor unique and appropriate sweat biomarkers in real-time and continuously during activity to allow individuals/subjects the ability to make informed decisions regarding hydration, nutrition, exertional status, and recovery. The biomarkers can be used in sensor systems such as wearable exercise tracking devices to provide for sweat collection and analytics to provide for event prediction and possible intervention based on the analyzed sweat samples.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A diagnostic method comprising:

non-invasively collecting at least one sweat sample from a biological subject undergoing physical activity and storing said sweat samples for a later analysis;

performing metabolic and proteomic profiling of biomarkers in the collected sweat sample;

comparing the metabolic and proteomic profile with a predetermined profile of the biomarkers;

determining a first physiological status of the of the biological subject from the biomarkers based on the comparison between the metabolic and proteomic profiles and predetermined profile of biomarkers;

comparing the first physiological status of the of the biological subject determined from the at least one sweat sample from the biological subject to a second physiological status of the of the biological subject determined from at least a second sweat sample.

2. The method of claim 1, further comprising:

freezing the sweat sample after collection.

3. The method of claim 1, wherein the physiological status comprises:

an identification of the biomarkers.

4. The method of claim 1, wherein the physiological status comprises:

an identification of diseases associated with the biomarkers.

5. The method of claim 1, wherein the physiological status comprises:

an identification of a health status of the biological subject based on a metabolic profile of the biomarkers in the collected sweat sample.

6. The method of claim 1, wherein the physiological status comprises:

An identification of a health status of the biological subject based on a proteomic profile of the biomarkers in the collected sweat sample.

7. The method of claim 1, further comprising:

correlating the physiological status with predetermined activity performance metrics associated with the biological subject.

8. The method of claim 1, wherein the metabolic profile includes biomarkers selected from the group consisting of proline, valine, threonine, leucine, isoleucine, and glutamic acid.

9. The method of claim 1, wherein the proteomic profile includes biomarkers selected from the group consisting of dermcidin, prolactin-inducible protein, zinc-alpha-2-glycoprotein, serum albumin, secretoglobin family 1D member 2, calcium-transporting ATPase type 2C member 2, mucin-like protein 1, clusterin, and desmoglein-1.

10. The method of claim 1, wherein the physiological status includes a physiological performance data.

11. The method of claim 1, wherein the physiological status includes a physiological performance data.

12. The method of claim 1, wherein the physiological status includes low blood sugar, malnourishment, dehydration, over-exertion, or a combination thereof.

13. The method of claim 1, further comprising:

perform a data analytics assessment based on the physiological status to determine a physiological event prediction of the biological subject.

* * * * *